US012791515B2

(12) United States Patent
Watanabe

(10) Patent No.: US 12,791,515 B2
(45) Date of Patent: Nov. 10, 2026

(54) GAS SENSOR

(71) Applicant: NGK INSULATORS, LTD., Nagoya (JP)

(72) Inventor: Yusuke Watanabe, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 105 days.

(21) Appl. No.: 18/961,877

(22) Filed: Nov. 27, 2024

(65) Prior Publication Data

US 2025/0093293 A1 Mar. 20, 2025

Related U.S. Application Data

(63) Continuation of application No. PCT/JP2023/021170, filed on Jun. 7, 2023.

(30) Foreign Application Priority Data

Jun. 22, 2022 (JP) ................................ 2022-100113

(51) Int. Cl.
*G01N 27/41* (2006.01)
*G01N 33/00* (2006.01)

(52) U.S. Cl.
CPC ......... *G01N 27/41* (2013.01); *G01N 33/0027* (2013.01)

(58) Field of Classification Search
CPC .. G01N 27/4065; G01N 27/41; G01N 27/419; G01N 33/0027
See application file for complete search history.

(56) References Cited

U.S. PATENT DOCUMENTS

2019/0277796 A1 9/2019 Kamada et al.
2020/0309729 A1* 10/2020 Watanabe .......... G01N 27/4076
(Continued)

FOREIGN PATENT DOCUMENTS

JP 10-38846 A 2/1998
JP 11-201931 A 7/1999
(Continued)

OTHER PUBLICATIONS

International Search Report of PCT/JP2023/021170 dated Aug. 22, 2023.

(Continued)

*Primary Examiner* — C. Sun
(74) *Attorney, Agent, or Firm* — MATTINGLY & MALUR, PC

(57) ABSTRACT

A gas sensor includes a sensor element and a control unit thereof. The sensor element includes: a base part; a measurement-object gas flow cavity; a reference gas chamber separated from the measurement-object gas flow cavity and closed inside the base part; a reference electrode disposed in the reference gas chamber; and a pump electrode disposed at a position different from the reference gas chamber. The control unit includes: a storing part storing in advance, a required amount of oxygen to be present in the reference gas chamber at a time at which oxygen concentration in the reference gas chamber is a predetermined concentration; and a processing part performing refresh processing in which a current is applied between the pump electrode and the reference electrode to pump out oxygen from the reference gas chamber, and then pump oxygen into the reference gas chamber in the required amount of the oxygen.

7 Claims, 11 Drawing Sheets

(56) References Cited

U.S. PATENT DOCUMENTS

| | | | | |
|---|---|---|---|---|
| 2021/0109058 | A1 | 4/2021 | Watanabe et al. | |
| 2021/0302354 | A1 | 9/2021 | Watanabe et al. | |
| 2021/0364465 | A1 * | 11/2021 | Azuma .................. | G01N 27/41 |

FOREIGN PATENT DOCUMENTS

| | | | |
|---|---|---|---|
| JP | 2007-278732 | A | 10/2007 |
| JP | 2019-158866 | A | 9/2019 |
| JP | 2021-156647 | A | 10/2021 |
| WO | 2020/004356 | A1 | 1/2020 |

OTHER PUBLICATIONS

Written Opinion of the International Searching Authority of PCT/JP2023/021170 dated Aug. 22, 2023.

International Preliminary Report on Patentability received in corresponding International Application No. PCT/JP2023/021170 dated Jan. 2, 2025.

* cited by examiner

GAS SENSOR

CROSS-REFERENCE TO RELATED APPLICATION

This application is a continuation application of PCT/JP2023/021170, filed on Jun. 7, 2023, which claims priority from Japanese Patent Application No. 2022-100113, filed on Jun. 22, 2022, the entire contents of which are incorporated herein by reference.

BACKGROUND OF THE INVENTION

Technical Field of the Invention

The present invention relates to a gas sensor for detecting a target gas to be measured in a measurement-object gas.

Background Art

A gas sensor is used for detection or measurement of concentration of an objective gas component (oxygen $O_2$, nitrogen oxide NOx, ammonia $NH_3$, hydrocarbon HC, carbon dioxide $CO_2$, etc.) in a measurement-object gas, such as exhaust gas of automobile. As such a gas sensor, a gas sensor which has a sensor element using an oxygen ion conductive solid electrolyte such as zirconia ($ZrO_2$) is known (for example, disclosed in JP 2021-156647 A, and WO 2020/004356 A1).

For example, JP 2021-156647 A discloses a sensor element including: an element body having, in its inside, a measurement-object gas flow part that introduces and flows a measurement-object gas and a reference gas chamber for storing a reference gas (e.g., air) as a reference for detecting the concentration of a specific gas in the measurement-object gas; and a reference electrode disposed in the reference gas chamber. JP 2021-156647 A also discloses that the reference gas chamber is independently provided inside the element body.

CITATION LIST

Patent Documents

Patent Document 1: JP 2021-156647 A
Patent Document 2: WO 2020/004356 A1

SUMMARY OF THE INVENTION

Problems to be Solved by the Invention

In the case of such a gas sensor, when the oxygen concentration in a reference gas around the reference electrode changes for any reason, the detection accuracy of a target gas to be measured in a measurement-object gas may reduce.

When the oxygen concentration in a measurement-object gas is known, as described in, for example, JP 2021-156647 A, the oxygen concentration in a reference gas can be determined by a potential difference between the reference electrode and an outer pump electrode disposed in a portion of the sensor element exposed to the measurement-object gas, and if necessary can be adjusted. For example, when the measurement-object gas is exhaust gas from a car or the like, the measurement-object gas at the time of fuel cutoff is an air atmosphere, and therefore the oxygen concentration is known.

However, the oxygen concentration in a measurement-object gas usually changes by the minute, and therefore the oxygen concentration in the reference gas chamber cannot be determined by the above method during time other than a specific timing when the oxygen concentration is known, such as the time of fuel cutoff described above. Therefore, during time other than such a specific timing when the oxygen concentration is known, even when the oxygen concentration in a reference gas changes, such a change cannot be detected so that the detection accuracy of a target gas to be measured in a measurement-object gas may reduce.

In light of this, it is an object of the present invention to provide a gas sensor that can prevent a reduction in the detection accuracy of the target gas to be measured in the measurement-object gas to maintain high detection accuracy.

Means for Solving the Problems

The present inventor has studied to correct a deviation of the oxygen concentration in a reference gas at any timing during the use of a gas sensor also in cases other than a case where the oxygen concentration in a measurement-object gas is known or irrespective of the oxygen concentration.

For example, WO 2020/004356 A1 discloses that a current is applied between a reference electrode and a measurement-object gas side electrode disposed in a portion exposed to a measurement-object gas to perform an oxygen pump-in control to pump oxygen into the surroundings of the reference electrode. Also, it is disclosed that in order to prevent a reduction in the detection accuracy of a target gas to be measured in a measurement-object gas, the concentration of a specific gas in the measurement-object gas is corrected based on a difference between a first base voltage across the reference electrode and the measurement-object gas side electrode when the oxygen pump-in control is not performed and a second base voltage across the reference electrode and the measurement-object gas side electrode when the oxygen pump-in control is performed. However, this correction is performed according to the amount of resistance change of the reference electrode due to deterioration with time, and is therefore not intended to be performed as a result of detection of a change in the oxygen concentration in a reference gas around the reference electrode.

The present inventor has intensively studied and as a result has found that by performing refresh processing of pumping out oxygen from a reference gas chamber to make oxygen in the reference gas chamber substantially zero, and then pumping oxygen into the reference gas chamber so that oxygen concentration in a reference gas in the reference gas chamber becomes a predetermined concentration, the oxygen concentration in the reference gas can be the predetermined concentration. The present inventor has found that by performing the refresh processing, the oxygen concentration in the reference gas around the reference electrode can be made (or, returned) to the predetermined concentration at any timing during the use of the gas sensor.

The present invention includes the following aspects.

(1) A gas sensor for detecting a target gas to be measured in a measurement-object gas, the gas sensor comprising a sensor element and a control unit for controlling the sensor element, wherein the sensor element comprises:

a base part in an elongated plate shape, including an oxygen-ion-conductive solid electrolyte layer;

a measurement-object gas flow cavity for introduction and flow of a measurement-object gas, formed from one end part in a longitudinal direction of the base part;

a reference gas chamber formed inside the base part, and being separated from the measurement-object gas flow cavity and closed inside the base part;

a reference electrode disposed in the reference gas chamber; and a pump electrode disposed at a position different from the reference gas chamber, and the control unit comprises:

a storing part storing in advance, a required amount of oxygen to be present in the reference gas chamber at a time at which oxygen concentration in a reference gas in the reference gas chamber is a predetermined concentration; and a processing part performing refresh processing in which a current is applied between the pump electrode and the reference electrode to pump out oxygen present in the reference gas chamber from the reference gas chamber, and then pump oxygen into the reference gas chamber in the required amount of the oxygen which is stored in advance by the storing part.

(2) The gas sensor according to the above (1), wherein the storing part stores in advance, as the required amount of the oxygen, a required current integrated value of a current flowing between the pump electrode and the reference electrode when the current is applied between the pump electrode and the reference electrode to move oxygen of the required amount of the oxygen, and in the refresh processing, the processing part pumps out oxygen present in the reference gas chamber from the reference gas chamber, and then applies the current between the pump electrode and the reference electrode until an integrated value of the current flowing between the pump electrode and the reference electrode reaches the required current integrated value to pump oxygen into the reference gas chamber in the required amount of the oxygen.

(3) The gas sensor according to the above (1), wherein the storing part stores in advance, as the required amount of the oxygen, a required time when a predetermined current is applied between the pump electrode and the reference electrode to move oxygen of the required amount of the oxygen, and in the refresh processing, the processing part pumps out oxygen present in the reference gas chamber from the reference gas chamber, and then applies the predetermined current between the pump electrode and the reference electrode for the required time to pump oxygen into the reference gas chamber in the required amount of the oxygen.

(4) The gas sensor according to the above (1), wherein the storing part stores in advance, as the required amount of the oxygen, a required current value when a current is applied between the pump electrode and the reference electrode for a predetermined time to move oxygen of the required amount of the oxygen, and in the refresh processing, the processing part pumps out oxygen present in the reference gas chamber from the reference gas chamber, and then applies the current of the required current value between the pump electrode and the reference electrode for the predetermined time to pump oxygen into the reference gas chamber in the required amount of the oxygen.

(5) The gas sensor according to any one of the above (1) to (4), wherein in the refresh processing, the processing part applies a predetermined voltage between the pump electrode and the reference electrode to make the current flow, and pumps out oxygen present in the reference gas chamber from the reference gas chamber until the current becomes at a predetermined value or less.

(6) The gas sensor according to any one of the above (1) to (4), wherein in the refresh processing, the processing part applies a predetermined voltage between the pump electrode and the reference electrode to make the current flow, and pumps out oxygen present in the reference gas chamber from the reference gas chamber until a change amount per time in the current becomes at a predetermined value or less.

(7) The gas sensor according to any one of the above (1) to (6), wherein a cycle for performing the refresh processing is determined based on a volume of the reference gas chamber.

(8) A control method of a gas sensor for detecting a target gas to be measured in a measurement-object gas, the gas sensor comprising a sensor element and a control unit for controlling the sensor element, wherein the sensor element comprises:

a base part in an elongated plate shape, including an oxygen-ion-conductive solid electrolyte layer;

a measurement-object gas flow cavity for introduction and flow of a measurement-object gas formed from one end part in a longitudinal direction of the base part;

a reference gas chamber formed inside the base part, and being separated from the measurement-object gas flow cavity and closed inside the base part;

a reference electrode disposed in the reference gas chamber; and a pump electrode disposed at a position different from the reference gas chamber, and the control unit comprises:

a storing part storing in advance, a required amount of oxygen to be present in the reference gas chamber at a time at which oxygen concentration in a reference gas in the reference gas chamber is a predetermined concentration; and a processing part performing refresh processing in which a current is applied between the pump electrode and the reference electrode to pump out oxygen present in the reference gas chamber from the reference gas chamber, and then pump oxygen in the required amount of the oxygen which is stored in advance by the storing part into the reference gas chamber, and the control method comprising:

a refresh processing step of applying a current between the pump electrode and the reference electrode by the processing part to pump out oxygen present in the reference gas chamber from the reference gas chamber, and then pumping oxygen of the required amount of the oxygen which is stored in advance by the storing part into the reference gas chamber by the processing part.

Advantageous Effect of the Invention

The use of the gas sensor according to the present invention makes it possible to make the oxygen concentration in the reference gas around the reference electrode a predetermined concentration at any timing during the use of the gas sensor also in cases other than a case where the oxygen concentration in a measurement-object gas is known or irrespective of the oxygen concentration. As a result, it is possible to prevent a reduction in the detection accuracy of the target gas to be measured to maintain high detection accuracy.

MODES FOR CARRYING OUT OF THE INVENTION

A gas sensor of the present invention includes a sensor element and a control unit for controlling the sensor element.

The sensor element contained in the gas sensor of the present invention includes:

- a base part in an elongated plate shape, including an oxygen-ion-conductive solid electrolyte layer;
- a measurement-object gas flow cavity for introduction and flow of a measurement-object gas formed from one end part in a longitudinal direction of the base part;
- a reference gas chamber formed inside the base part, and being separated from the measurement-object gas flow cavity and closed inside the base part;
- a reference electrode disposed in the reference gas chamber; and a pump electrode disposed at a position different from the reference gas chamber.

The control unit contained in the gas sensor of the present invention includes:

- a storing part storing in advance, a required amount of oxygen to be present in the reference gas chamber at a time at which oxygen concentration in a reference gas in the reference gas chamber is a predetermined concentration; and
- a processing part performing refresh processing in which a current is applied between the pump electrode and the reference electrode to pump out oxygen present in the reference gas chamber from the reference gas chamber, and then pump oxygen into the reference gas chamber in the required amount of the oxygen which is stored in advance by the storing part.

Schematic Configuration of Gas Sensor

Figure 1:
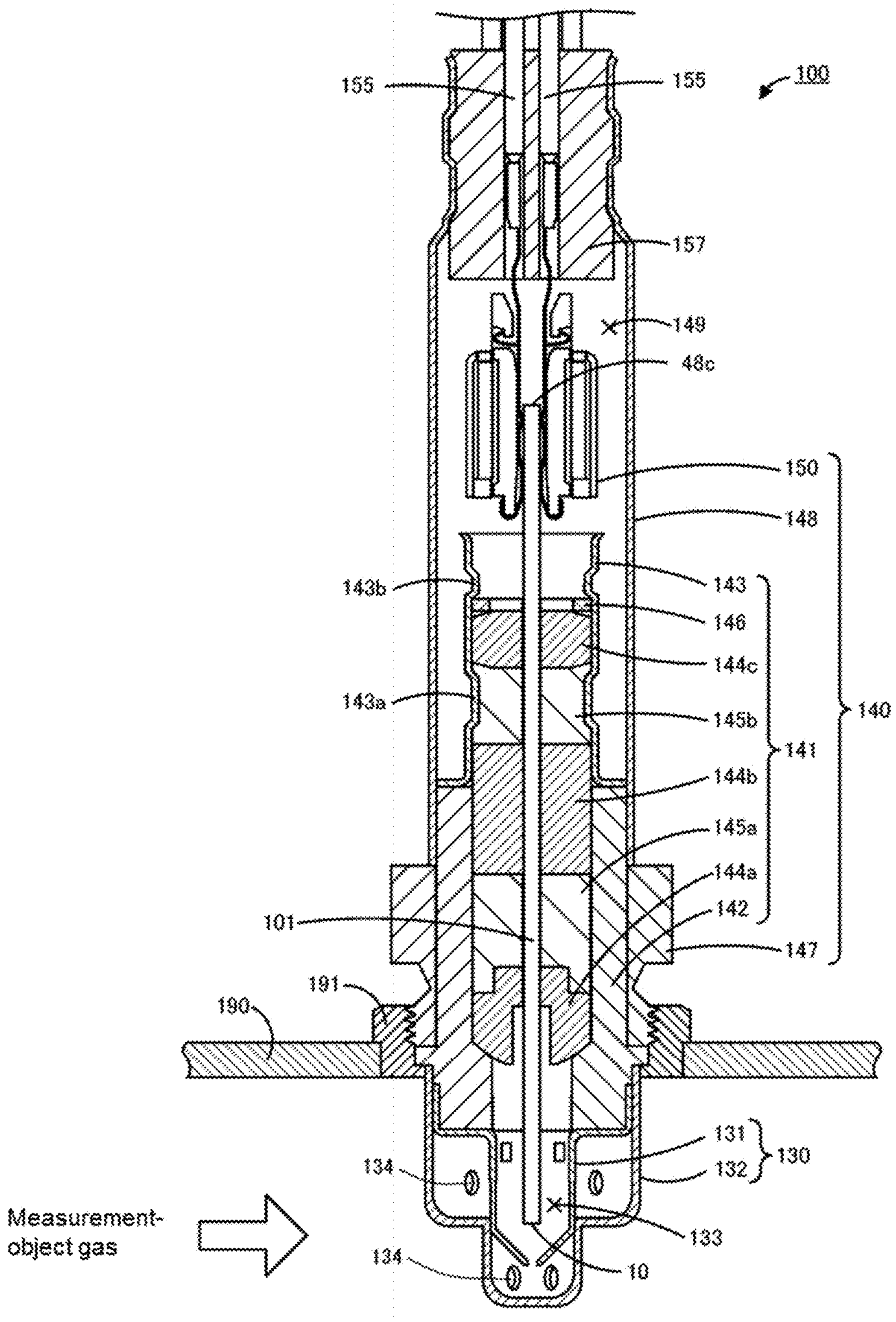
FIG. 1 is a vertical sectional view schematically showing one example of the schematic configuration of a gas sensor 100.
Figure 2:
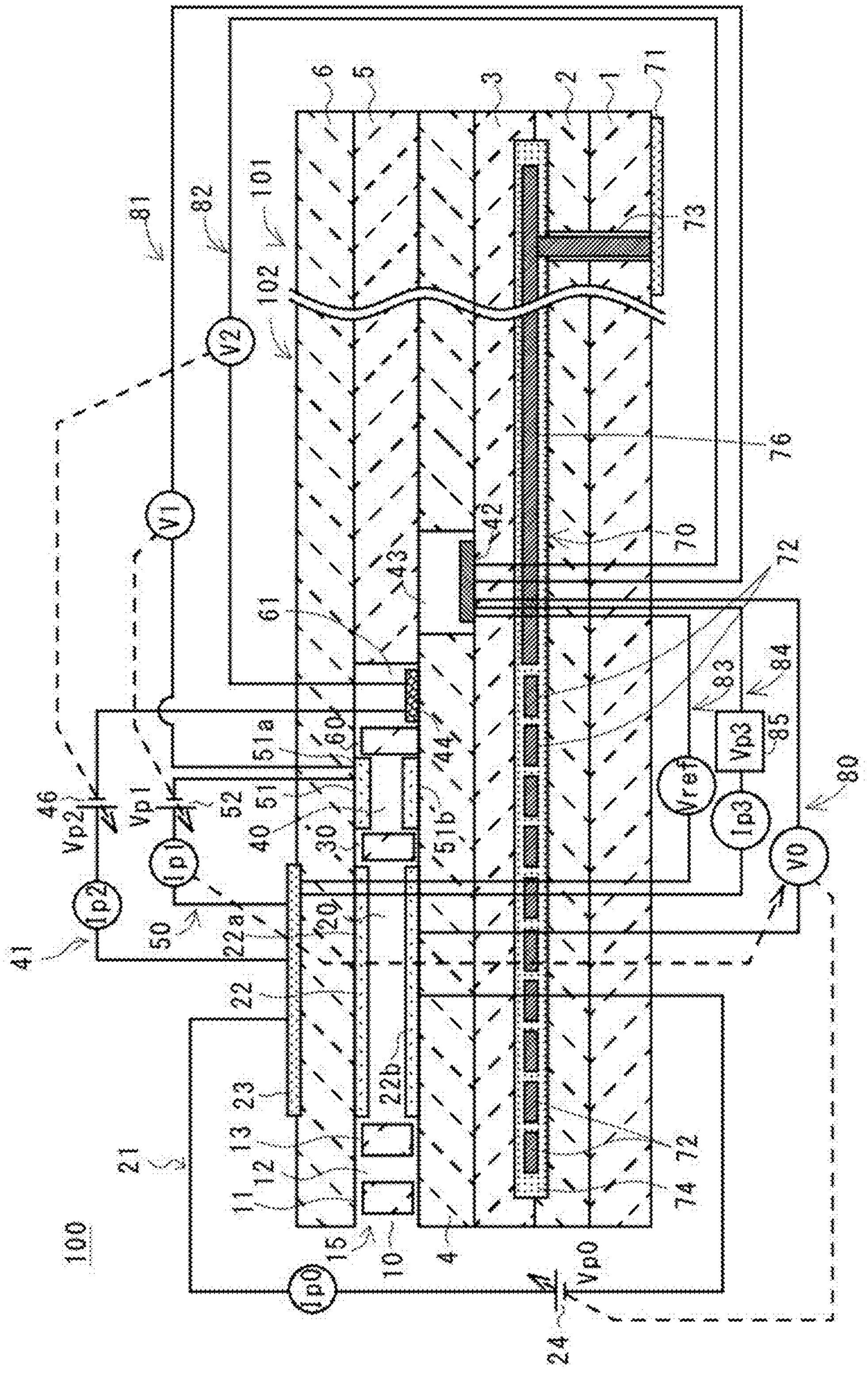
FIG. 2 is a vertical sectional schematic view in a longitudinal direction of a sensor element 101, which shows one example of the schematic configuration of the gas sensor 100.
Figure 3:
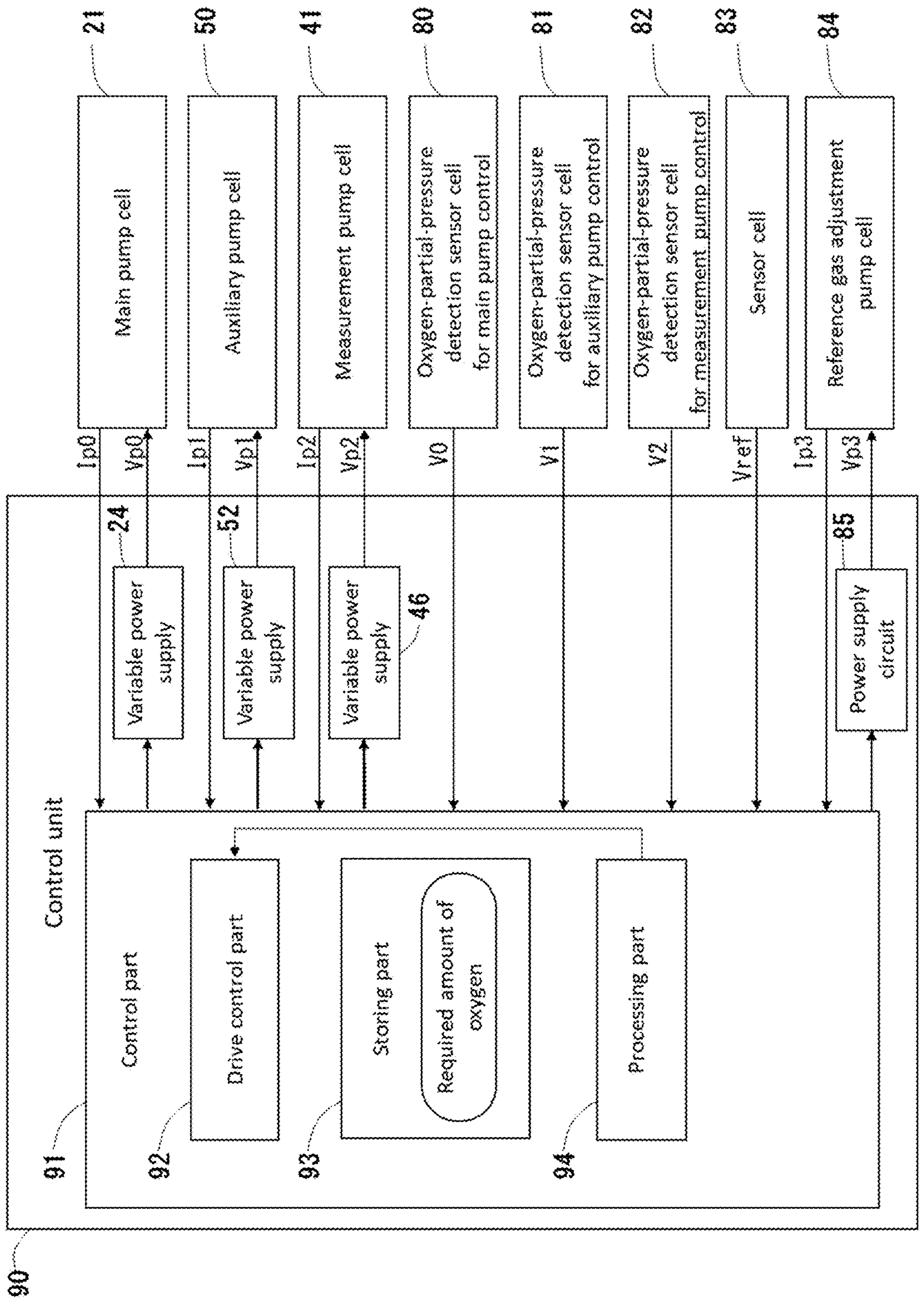
FIG. 3 is a block diagram showing electric connections between a control unit 90, and respective pump cells 21, 50, 41 and 84, and respective sensor cells 80, 81, 82, and 83 of the sensor element 101.

The gas sensor according to the present invention will be described below with reference to the drawings. FIG. 1 is a vertical sectional view schematically showing one example of the schematic configuration of a gas sensor 100 according to an embodiment of the present invention. FIG. 2 is a vertical sectional schematic view in a longitudinal direction of a sensor element 101, which shows one example of the schematic configuration of the gas sensor 100. FIG. 3 is a block diagram showing an example of electrical connections between a control unit 90 and the sensor element 101. Hereinafter, based on FIG. 2, the upper side and the lower side in FIG. 2 are respectively defined as top and bottom, and the left side and the right side in FIG. 2 are respectively defined as a front end side and a rear end side. The left side, right side, lower side, and upper side of FIG. 1 respectively correspond to top, bottom, front end side, and rear end side defined based on FIG. 2. It is noted that the structure of the gas sensor shown in FIG. 1 is well known and disclosed in, for example, JP 2021-156647 A and WO 2020/004356 A1.

As shown in FIG. 1, the gas sensor 100 includes a sensor element 101, a protection cover 130 to protect the front end side of the sensor element 101, and a sensor assembly 140 including a connector 150 electrically connected with the sensor element 101. As shown in FIG. 1, for example, this gas sensor 100 is attached to a pipe 190 such as an exhaust gas pipe of a vehicle and used to measure the concentration of a target gas to be measured, such as NOx, $NH_3$, or $O_2$, contained in exhaust gas as a measurement-object gas. In the present embodiment, the gas sensor 100 measures the concentration of NOx as a target gas to be measured.

The protection cover 130 includes a bottomed cylindrical inner protection cover 131 to cover the front end of the sensor element 101 and a bottomed cylindrical outer protection cover 132 to cover the inner protection cover 131. The inner protection cover 131 and the outer protection cover 132 have a plurality of holes 134 formed to flow a measurement-object gas into the protection cover 130. A sensor element chamber 133 is formed as a space surrounded by the inner protection cover 131, and the front end of the sensor element 101 is disposed in this sensor element chamber 133.

The sensor assembly 140 includes an element sealing body 141 to seal and fix the sensor element 101, a nut 147 and an outer cylinder 148 attached to the element scaling body 141, and a connector 150 that is in contact with and electrically connected with connector electrodes (which are not shown, but only a heater connector electrode 71 described later is shown in FIG. 2) formed on the surface (upper and lower surfaces) of the rear end of the sensor element 101.

The element sealing body 141 includes a cylindrical main fitting 142, a cylindrical inner cylinder 143 coaxially fixed to the main fitting 142 by welding, and ceramic supporters 144*a* to 144*c*, green compacts 145*a* and 145*b*, and a metal ring 146 encapsulated in a through-hole inside the main fitting 142 and the inner cylinder 143. The sensor element 101 is located on the central axis of the element sealing body 141 and extends through the element sealing body 141 in the front and rear direction. The inner cylinder 143 has a reduced diameter portion 143a for pressing the green compact 145b toward the central axis of the inner cylinder 143 and a reduced diameter portion 143b for pressing forward the ceramic supporters 144a to 144c and the green compacts 145a and 145b via the metal ring 146. The green compacts 145a and 145b are compressed between both the main fitting 142 and the inner cylinder 143 and the sensor element 101 by pressing force from the reduced diameter portions 143a and 143b, and therefore the green compacts 145a and 145b seal the sensor element chamber 133 in the protection cover 130 and a space 149 in the outer cylinder 148 from each other and fix the sensor element 101.

The nut 147 is concentrically fixed to the main fitting 142 and has an external thread formed on an outer peripheral surface thereof. The external thread of the nut 147 is inserted in a fixing member 191 welded to the pipe 190 and having an internal thread in an inner peripheral surface thereof. Thus, the gas sensor 100 is fixed to the pipe 190 in a state where part of the gas sensor 100 such as the front end of the sensor element 101 and the protection cover 130 protrudes into the pipe 190.

The external cylinder 148 surrounds the inner cylinder 143, the sensor element 101, and the connector 150, and a plurality of lead wires 155 connected to the connector 150 are drawn outside from the rear end. These lead wires 155 are electrically connected with electrodes (described later) of the sensor element 101 respectively via the connector 150. A gap between the outer cylinder 148 and the lead wires 155 is sealed with a rubber plug 157. The space 149 in the outer cylinder 148 is filled with air. The rear end of the sensor element 101 is disposed in this space 149.

(Sensor Element)

As shown in FIG. 2, the sensor element 101 is an element in an elongated plate shape, including a base part 102 having such a structure that a plurality of oxygen-ion-conductive solid electrolyte layers are layered. The elongated plate shape also called a long plate shape or a belt shape. The base part 102 has such a structure that six layers, namely, a first substrate layer 1, a second substrate layer 2, a third substrate layer 3, a first solid electrolyte layer 4, a spacer layer 5, and a second solid electrolyte layer 6, are layered in this order from the bottom side, as viewed in the drawing. Each of the six layers is formed of an oxygen-ion-conductive solid electrolyte layer containing, for example, zirconia ($ZrO_2$). The solid electrolyte forming these six layers is dense and gastight. These six layers all may have the same thickness, or the thickness may vary among the layers. The layers are adhered to each other with an adhesive layer of a solid electrolyte interposed therebetween, and the base part 102 includes the adhesive layer. While a layer configuration composed of the six layers is illustrated in FIG. 2, the layer configuration in the present invention is not limited to this, and any number of layers and any layer configuration are possible.

The sensor element 101 is manufactured, for example, by stacking ceramic green sheets corresponding to the individual layers after conducting predetermined processing, printing of circuit pattern and the like, and then firing the stacked ceramic green sheets so that they are combined together.

A gas inlet 10 is formed between the lower surface of the second solid electrolyte layer 6 and the upper surface of the first solid electrolyte layer 4 in one end part in the longitudinal direction (hereinafter, referred to as a front end part) of the sensor element 101. A measurement-object gas flow cavity 15, that is, a measurement-object gas flow part is formed in such a form that a first diffusion-rate limiting part 11, a buffer space 12, a second diffusion-rate limiting part 13, a first internal cavity 20, a third diffusion-rate limiting part 30, a second internal cavity 40, a fourth diffusion-rate limiting part 60, and a third internal cavity 61 communicate in this order in the longitudinal direction from the gas inlet 10.

The gas inlet 10, the buffer space 12, the first internal cavity 20, the second internal cavity 40, and the third internal cavity 61 constitute internal spaces of the sensor element 101. Each of the internal spaces is provided in such a manner that a portion of the spacer layer 5 is hollowed out, and the top of each of the internal spaces is defined by the lower surface of the second solid electrolyte layer 6, the bottom of each of the internal spaces is defined by the upper surface of the first solid electrolyte layer 4, and the lateral surface of each of the internal spaces is defined by the lateral surface of the spacer layer 5.

Each of the first diffusion-rate limiting part 11, the second diffusion-rate limiting part 13, and the third diffusion-rate limiting part 30 is provided as two laterally elongated slits (having the longitudinal direction of the openings in the direction perpendicular to the figure in FIG. 2). Each of the first diffusion-rate limiting part 11, the second diffusion-rate limiting part 13, and the third diffusion-rate limiting part 30 may be in such a form that a desired diffusion resistance is created, but the form is not limited to the slits.

The fourth diffusion-rate limiting part 60 is provided as a single laterally elongated slit (having the longitudinal direction of the opening in the direction perpendicular to the figure in FIG. 2) between the spacer layer 5 and the second solid electrolyte layer 6. The fourth diffusion-rate limiting part 60 may be in such a form that a desired diffusion resistance is created, but the form is not limited to the slit.

Between the lower surface of the spacer layer 5 and the upper surface of the third substrate layer 3, a reference gas chamber 43 is provided. The reference gas chamber 43 is a space inside the sensor element 101 and is provided by hollowing out the first solid electrolyte layer 4. The reference gas chamber 43 is formed inside the base part 102, and being separated from the measurement-object gas flow cavity 15. The reference gas chamber 43 is a space closed inside the base part 102. The reference gas chamber 43 is a region for storing a reference gas used as a reference when the concentration of NOx is measured. The reference gas is a gas having a predetermined oxygen concentration. In the present embodiment, the reference gas is air or a gas having the same oxygen concentration as air (e.g., a gas containing nitrogen as a base gas and oxygen). In the reference gas chamber 43, a reference electrode 42 is disposed.

The reference electrode 42 is an electrode disposed on the upper surface of the third substrate layer 3 in the reference gas chamber 43. As will be described later, the reference electrode 42 can be used to measure the oxygen concentration (oxygen partial pressure) in the first internal cavity 20, the second internal cavity 40, and the third internal cavity 61. The reference electrode 42 is formed as a porous cermet electrode (e.g., a cermet electrode of Pt and $ZrO_2$).

In the measurement-object gas flow cavity 15, the gas inlet 10 is open to the external space, and the measurement-object gas is taken into the sensor element 101 from the external space through the gas inlet 10.

In the present embodiment, the measurement-object gas flow cavity 15 is in such a form that the measurement-object gas is introduced through the gas inlet 10 that is open on the front end surface of the sensor element 101, however, the present invention is not limited to this form. For example, the measurement-object gas flow cavity 15 need not have a recess of the gas inlet 10. In this case, the first diffusion-rate limiting part 11 substantially serves as a gas inlet.

For example, the measurement-object gas flow cavity 15 may have an opening that communicates with the buffer space 12 or a position in the vicinity of the buffer space 12 of the first internal cavity 20, on a lateral surface along the longitudinal direction of the base part 102. In this case, the measurement-object gas is introduced from the lateral surface along the longitudinal direction of the base part 102 through the opening.

Further, for example, the measurement-object gas flow cavity 15 may be so configured that the measurement-object gas is introduced through a porous body.

The first diffusion-rate limiting part 11 creates a predetermined diffusion resistance to the measurement-object gas taken through the gas inlet 10.

The buffer space 12 is provided to guide the measurement-object gas introduced from the first diffusion-rate limiting part 11 to the second diffusion-rate limiting part 13.

The second diffusion-rate limiting part 13 creates a predetermined diffusion resistance to the measurement-object gas introduced into the first internal cavity 20 from the buffer space 12.

It suffices that the amount of the measurement-object gas to be introduced into the first internal cavity 20 finally falls within a predetermined range. That is, it suffices that a predetermined diffusion resistance is created in a whole from the front end part of the sensor element 101 to the second diffusion-rate limiting part 13. For example, the first diffusion-rate limiting part 11 may directly communicate with the first internal cavity 20, or the buffer space 12 and the second diffusion-rate limiting part 13 may be absent.

The buffer space 12 is provided to mitigate the influence of pressure fluctuation on the detected value when the pressure of the measurement-object gas fluctuates.

When the measurement-object gas is introduced from outside the sensor element 101 into the first internal cavity 20, the measurement-object gas, which is rapidly taken through the gas inlet 10 into the sensor element 101 due to pressure fluctuation of the measurement-object gas in the external space (pulsations in exhaust pressure if the measurement-object gas is automotive exhaust gas), is not directly introduced into the first internal cavity 20. Rather, the measurement-object gas is introduced into the first internal cavity 20 after the pressure fluctuation of the measurement-object gas is eliminated through the first diffusion-rate limiting part 11, the buffer space 12, and the second diffusion-rate limiting part 13. Thus, the pressure fluctuation of the measurement-object gas introduced into the first internal cavity 20 becomes almost negligible.

The first internal cavity 20 is provided as a space for adjusting the oxygen partial pressure in the measurement-object gas introduced through the second diffusion-rate limiting part 13. The oxygen partial pressure is adjusted by operation of a main pump cell 21.

The main pump cell 21 is an electrochemical pump cell composed of an inner main pump electrode 22 having a ceiling electrode portion 22*a* disposed over substantially the entire surface of the lower surface of the second solid electrolyte layer 6 that faces the first internal cavity 20, an outer pump electrode 23 disposed on a region of the upper surface of the second solid electrolyte layer 6 that corresponds to the ceiling electrode portion 22*a* so as to be exposed to the external space (the sensor element chamber 133 in FIG. 1), and the second solid electrolyte layer 6 sandwiched between the inner main pump electrode 22 and the outer pump electrode 23.

The inner main pump electrode 22 is disposed facing the first internal cavity 20. That is, the inner main pump electrode 22 is formed to span the upper and lower solid electrolyte layers (the second solid electrolyte layer 6 and the first solid electrolyte layer 4) that define the first internal cavity 20 and the spacer layer 5 that defines the lateral wall. Specifically, the ceiling electrode portion 22*a* is formed on the lower surface of the second solid electrolyte layer 6 that defines the ceiling surface of the first internal cavity 20, and a bottom electrode portion 22*b* is formed on the upper surface of the first solid electrolyte layer 4 that defines the bottom surface of the first internal cavity 20. Also, lateral electrode portions (not shown) are formed on the lateral wall surfaces (inner surface) of the spacer layer 5 that form both lateral wall parts of the first internal cavity 20 so as to connect the ceiling electrode portion 22*a* and the bottom electrode portion 22*b*. Thus, the inner main pump electrode 22 is provided as a tunnel-like structure in the area where the lateral electrode portions are disposed.

The inner main pump electrode 22 and the outer pump electrode 23 are each formed as a porous cermet electrode (e.g., a cermet electrode of Pt containing 1% Au and $ZrO_2$). It is to be noted that the inner main pump electrode 22 to be in contact with the measurement-object gas is formed using a material having a weakened ability to reduce a NOx component in the measurement-object gas.

In the main pump cell 21, a desired pump voltage Vp0 is applied between the inner main pump electrode 22 and the outer pump electrode 23 by a variable power supply 24 to flow a pump current Ip0 between the inner main pump electrode 22 and the outer pump electrode 23 in either a positive or negative direction, and thus it is possible to pump out oxygen in the first internal cavity 20 to the external space or pump oxygen into the first internal cavity 20 from the external space.

To detect the oxygen concentration (oxygen partial pressure) in the atmosphere in the first internal cavity 20, the inner main pump electrode 22, the second solid electrolyte layer 6, the spacer layer 5, the first solid electrolyte layer 4, the third substrate layer 3, and the reference electrode 42 form an electrochemical sensor cell, namely, an oxygen-partial-pressure detection sensor cell 80 for main pump control.

The oxygen concentration (oxygen partial pressure) in the first internal cavity 20 can be detected from an electromotive force (a voltage V0) measured in the oxygen-partial-pressure detection sensor cell 80 for main pump control. In addition, the pump current Ip0 is controlled by performing feedback control of the pump voltage Vp0 so that the voltage V0 is constant. Thus, the oxygen concentration in the first internal cavity 20 can be maintained at a predetermined constant value.

The third diffusion-rate limiting part 30 creates a predetermined diffusion resistance to the measurement-object gas whose oxygen concentration (oxygen partial pressure) has been controlled in the first internal cavity 20 by the operation of the main pump cell 21, and guides the measurement-object gas into the second internal cavity 40.

The second internal cavity 40 is provided as a space for adjusting the oxygen partial pressure in the measurement-object gas introduced through the third diffusion-rate limiting part 30 more accurately. The oxygen partial pressure is adjusted by operation of an auxiliary pump cell 50.

After the oxygen concentration (oxygen partial pressure) in the measurement-object gas is adjusted in advance in the first internal cavity 20, the measurement-object gas is introduced through the third diffusion-rate limiting part 30, and is further subjected to adjustment of the oxygen partial pressure by the auxiliary pump cell 50 in the second internal cavity 40. Thus, the oxygen concentration in the second internal cavity 40 can be kept constant with high accuracy, and the NOx concentration can be measured with high accuracy in the gas sensor 100.

The auxiliary pump cell 50 is an auxiliary electrochemical pump cell composed of an auxiliary pump electrode 51 having a ceiling electrode portion 51*a* disposed on substantially the entire surface of lower surface of the second solid electrolyte layer 6 facing with the second internal cavity 40, the outer pump electrode 23 (the outer electrode is not limited to the outer pump electrode 23, but may be any suitable electrode disposed at a position different from the measurement-object gas flow cavity 15), and the second solid electrolyte layer 6.

The auxiliary pump electrode 51 is disposed at a position farther from the one end part (the front end portion) in the longitudinal direction of the base part 102 (the sensor element 101) than the inner main pump electrode 22 on the inner surface of the measurement-object gas flow cavity 15.

This auxiliary pump electrode 51 is disposed in the second internal cavity 40 in a tunnel-like structure similar to the inner main pump electrode 22 disposed in the first internal cavity 20 described previously. Specifically, in the tunnel-like structure, the ceiling electrode portion 51*a* is formed on the second solid electrolyte layer 6 that defines the ceiling surface of the second internal cavity 40, a bottom electrode portion 51*b* is formed on the first solid electrolyte layer 4 that defines the bottom surface of the second internal cavity 40, and lateral electrode portions (not shown) connecting the ceiling electrode portion 51*a* and the bottom electrode portion 51*b* are formed on the wall surfaces of the spacer layer 5 that define the lateral walls of the second internal cavity 40.

It is to be noted that the auxiliary pump electrode 51 is formed using a material having a weakened ability to reduce a NOx component in the measurement-object gas, as with the case of the inner main pump electrode 22.

In the auxiliary pump cell 50, by applying a desired pump voltage Vp1 between the auxiliary pump electrode 51 and the outer pump electrode 23 by a variable power supply 52, it is possible to pump out oxygen in the atmosphere in the second internal cavity 40 to the external space, or pump the oxygen into the second internal cavity 40 from the external space.

To control the oxygen partial pressure in the atmosphere in the second internal cavity 40, the auxiliary pump electrode 51, the reference electrode 42, the second solid electrolyte layer 6, the spacer layer 5, the first solid electrolyte layer 4, and the third substrate layer 3 constitute an electrochemical sensor cell, namely, an oxygen-partial-pressure detection sensor cell 81 for auxiliary pump control.

The auxiliary pump cell 50 performs pumping with the variable power supply 52 whose voltage is controlled on the basis of an electromotive force (a voltage V1) detected by the oxygen-partial-pressure detection sensor cell 81 for auxiliary pump control. Thus, the oxygen partial pressure in the atmosphere in the second internal cavity 40 is controlled to such a low partial pressure that does not substantially affect measurement of NOx.

In addition, a pump current Ip1 is used for control of the voltage V0 of the oxygen-partial-pressure detection sensor cell 80 for main pump control. Specifically, the pump current Ip1 is input to the oxygen-partial-pressure detection sensor cell 80 for main pump control as a control signal to control the voltage V0, and thus the gradient of the oxygen partial pressure in the measurement-object gas introduced into the second internal cavity 40 from the third diffusion-rate limiting part 30 is controlled to remain constant. In using as a NOx sensor, the oxygen concentration in the second internal cavity 40 is kept at a constant value of about 0.001 ppm by the actions of the main pump cell 21 and the auxiliary pump cell 50.

The fourth diffusion-rate limiting part 60 creates a predetermined diffusion resistance to the measurement-object gas whose oxygen concentration (oxygen partial pressure) has been controlled to further low in the second internal cavity 40 by the operation of the auxiliary pump cell 50, and guides the measurement-object gas into the third internal cavity 61.

The third internal cavity 61 is provided as a space for measuring nitrogen oxide (NOx) concentration in the measurement-object gas introduced through the fourth diffusion-rate limiting part 60. By the operation of a measurement pump cell 41, NOx concentration is measured.

The measurement pump cell 41 measures NOx concentration in the measurement-object gas in the third internal cavity 61. The measurement pump cell 41 includes an inner measurement electrode (in this embodiment, a measurement electrode 44) disposed in the measurement-object gas flow cavity 15 (on the inner surface of the measurement-object gas flow cavity 15) and an outer measurement electrode (in this embodiment, the outer pump electrode 23) disposed at a position different from the measurement-object gas flow cavity 15 on the base part and corresponding to the inner measurement electrode.

That is, in this embodiment, the measurement pump cell 41 is an electrochemical pump cell composed of the measurement electrode 44 disposed on the upper surface of the first solid electrolyte layer 4 facing with the third internal cavity 61, the outer pump electrode 23 (the outer electrode is not limited to the outer pump electrode 23, but may be any suitable electrode disposed at a position different from the measurement-object gas flow cavity 15), the second solid electrolyte layer 6, the spacer layer 5, and the first solid electrolyte layer 4.

The measurement electrode 44 is disposed at a position farther from the one end part (the front end portion) in the longitudinal direction of the base part 102 (the sensor element 101) than the inner main pump electrode 22 and the auxiliary pump electrode 51 on the inner surface of the measurement-object gas flow cavity 15.

The measurement electrode 44 is a porous cermet electrode. The measurement electrode 44 functions also as a NOx reduction catalyst that reduces NOx present in the atmosphere in the third internal cavity 61. For example, in this embodiment, the measurement electrode 44 is formed as a porous cermet electrode made of Pt and Rh, and $ZrO_2$.

In the measurement pump cell 41, oxygen generated by decomposition of nitrogen oxide in the atmosphere around the measurement electrode 44 is pumped out, and the amount of generated oxygen can be detected as a pump current Ip2.

To detect the oxygen partial pressure around the measurement electrode 44, the first solid electrolyte layer 4, the third substrate layer 3, the measurement electrode 44, and the reference electrode 42 constitute an electrochemical sensor cell, namely an oxygen-partial-pressure detection sensor cell 82 for measurement pump control. A variable power supply 46 is controlled on the basis of an electromotive force (a voltage V2) detected by the oxygen-partial-pressure detection sensor cell 82 for measurement pump control.

The measurement-object gas introduced into the second internal cavity 40 reaches the measurement electrode 44 in the third internal cavity 61 through the fourth diffusion-rate limiting part 60 under the condition that the oxygen partial pressure is controlled. Nitrogen oxide in the measurement-object gas around the measurement electrode 44 is reduced ($2NO \rightarrow N_2+O_2$) to generate oxygen. The generated oxygen is to be pumped by the measurement pump cell 41, and at this time, a pump voltage Vp2 of the variable power supply 46 is controlled so that the voltage V2 detected by the oxygen-partial-pressure detection sensor cell 82 for measurement pump control is constant. Since the amount of oxygen generated around the measurement electrode 44 is proportional to the concentration of nitrogen oxide in the measurement-object gas, nitrogen oxide concentration in the measurement-object gas is calculated by using the pump current Ip2 in the measurement pump cell 41.

By configuring oxygen partial pressure detecting means by an electrochemical sensor cell composed of a combination of the measurement electrode 44, the first solid electrolyte layer 4, the third substrate layer 3 and the reference electrode 42, it is possible to detect an electromotive force in accordance with a difference between the amount of oxygen generated by reduction of NOx components in the atmosphere around the measurement electrode 44 and the amount of oxygen contained in the reference air, and hence it is possible to determine the concentration of NOx components in the measurement-object gas.

Also, the second solid electrolyte layer 6, the spacer layer 5, the first solid electrolyte layer 4, the third substrate layer 3, the outer pump electrode 23, and the reference electrode 42 constitute an electrochemical sensor cell 83, and it is possible to detect the oxygen partial pressure in the measurement-object gas outside the sensor by an electromotive force (a voltage Vref) obtained by the sensor cell 83.

Further, the second solid electrolyte layer 6, the spacer layer 5, the first solid electrolyte layer 4, the third substrate layer 3, the outer pump electrode 23, and the reference electrode 42 constitute an electrochemical reference gas adjustment pump cell 84. The reference gas adjustment pump cell 84 pumps oxygen by a pump current Ip3 flowing due to a pump voltage Vp3 applied by a power supply circuit 85 that is connected between the outer pump electrode 23 and the reference electrode 42. Thus, the reference gas adjustment pump cell 84 can pump oxygen into a space around the reference electrode 42, that is, the reference gas chamber 43 from a space around the outer pump electrode 23 (the sensor element chamber 133 in FIG. 1), or pump out oxygen from the reference gas chamber 43 to the space around the outer pump electrode 23.

In the gas sensor 100 having such a configuration, the main pump cell 21 and the auxiliary pump cell 50 are operated to supply a measurement-object gas whose oxygen partial pressure is usually kept at a low constant value (the value that does not substantially affect measurement of NOx) to the measurement pump cell 41. Therefore, NOx concentration in the measurement-object gas can be detected on the basis of the pump current Ip2 that flows as a result of pumping out of the oxygen generated by reduction of NOx by the measurement pump cell 41 and is almost in proportion to the concentration of NOx in the measurement-object gas.

The sensor element 101 further includes a heater part 70 that functions as a temperature regulator of heating and maintaining the temperature of the sensor element 101 so as to enhance the oxygen ion conductivity of the solid electrolyte. The heater part 70 includes a heater connector electrode 71, a heater 72, a heater lead 76, a through hole 73, and a heater insulating layer 74.

The heater connector electrode 71 is an electrode formed in contact with the lower surface of the first substrate layer 1. The power can be supplied to the heater part 70 from the outside by connecting the heater connector electrode 71 with a heater power supply that is an external power supply.

The heater 72 is an electrical resistor sandwiched by the second substrate layer 2 and the third substrate layer 3 from top and bottom. The heater 72 is connected with the heater connector electrode 71 via a heater lead 76 that connects with the heater 72 and extends in the rear end side in the longitudinal direction of the sensor element 101, and the through hole 73. The heater 72 is externally powered through the heater connector electrode 71 to generate heat, and heats and maintains the temperature of the solid electrolyte forming the sensor element 101.

The heater 72 is embedded over the whole area from the first internal cavity 20 to the third internal cavity 61 so that the temperature of the sensor element 101 can be adjusted to such a temperature that activates the solid electrolyte. The temperature may be adjusted so that the main pump cell 21, the auxiliary pump cell 50, and the measurement pump cell 41 are operable. It is not necessary that the whole area is adjusted to the same temperature, but the sensor element 101 may have temperature distribution.

In the sensor element 101 of the present embodiment, the heater 72 is embedded in the base part 102, but this form is not limitative. The heater 72 may be disposed to heat the base part 102. That is, the heater 72 may heat the sensor element 101 to develop oxygen ion conductivity with which the main pump cell 21, the auxiliary pump cell 50, and the measurement pump cell 41 are operable. For example, the heater 72 may be embedded in the base part 102 as in the present embodiment. Alternatively, for example, the heater part 70 may be formed as a heater substrate that is separate from the base part 102, and may be disposed at a position adjacent to the base part 102. Alternatively, the sensor element 101 may be heated by a measurement-object gas at high temperature. For accurate measurement, it is preferred that the temperature of the sensor element 101 be constant regardless of the temperature of the measurement-object gas. In consideration of this point, it is preferred that the sensor element 101 include the heater part 70 as in the present embodiment.

The heater insulating layer 74 is formed of an insulator such as alumina on the upper and lower surfaces of the heater 72 and the heater lead 76. The heater insulating layer 74 is formed to ensure electrical insulation between the second substrate layer 2, and the heater 72 and the heater lead 76, and electrical insulation between the third substrate layer 3, and the heater 72 and the heater lead 76.

(Control Unit)

The gas sensor 100 of this embodiment includes the sensor element 101 described above and the control unit 90 for controlling the sensor element 101. In the gas sensor 100, each of the electrodes 22, 23, 51, 44, and 42 of the sensor element 101 is electrically connected to the control unit 90 through the lead wire 155. FIG. 3 is a block diagram showing electric connections between the control unit 90, and the respective pump cells 21, 50, 41 and 84, and the respective sensor cells 80, 81, 82, and 83 of the sensor element 101 in this embodimet. The control unit 90 includes the above-described variable power supplies 24, 46, and 52 and the power supply circuit 85 and a control part 91. The control part 91 includes a drive control part 92, a storing part 93, and a processing part 94.

The control part 91 is realized by a general-purpose or dedicated computer, and functions as the drive control part 92, the storing part 93, and the processing part 94 are realized by a CPU, a memory or the like installed in the computer. It is to be noted that when NOx contained in exhaust gas from the engine of a car is a target gas to be measured by the gas sensor 100 and the sensor element 101 is attached to an exhaust gas path, some or all of the functions of the control unit 90 (especially, the control part 91) may be realized by an electronic control unit (ECU) installed in the car.

The control part 91 is configured to acquire an electromotive force (a voltage V0, V1, V2, or Vref) in each of the sensor cells 80, 81, 82, and 83, and a pump current (Ip0, Ip1, Ip2, or Ip3) in each of the pump cells 21, 50, 41 and 84 of the sensor element 101. Further, the control part 91 is configured to output control signals to the variable power supplies 24, 52 and 46, and the power supply circuit 85.

The drive control part 92 is configured to control the operation of the main pump cell 21, the auxiliary pump cell 50 and the measurement pump cell 41. Further, the drive control part 92 may be configured to control the operation of the reference gas adjustment pump cell 84.

The drive control part 92 performs a normal control for detecting a target gas to be measured in a measurement-object gas by operating at least the measurement pump cell 41 including the inner measurement electrode (the measurement electrode 44) disposed on the inner surface of the measurement-object gas flow cavity 15.

In the present embodiment, the drive control part 92 operates the main pump cell 21, the auxiliary pump cell 50, and the measurement pump cell 41 in the normal control. More specifically, in the present embodiment, the normal control is performed in the following manner.

In the normal control, the drive control part 92 performs feedback control of the pump voltage Vp0 of the variable power supply 24 in the main pump cell 21 so that the voltage V0 in the oxygen-partial-pressure detection sensor cell 80 for main pump control is at a constant value (referred to as a set value $V0_{SET}$). The voltage V0 indicates the oxygen partial pressure in the vicinity of the inner main pump electrode 22, and therefore making the voltage V0 constant means that the oxygen partial pressure in the vicinity of the inner main pump electrode 22 is made constant. As a result, the pump current Ip0 in the main pump cell 21 varies depending on the oxygen concentration in the measurement-object gas.

When the oxygen partial pressure in the measurement-object gas is higher than the oxygen partial pressure corresponding to the set value $V0_{SET}$, the main pump cell 21 pumps oxygen out from the first internal cavity 20. On the other hand, when the oxygen partial pressure in the measurement-object gas is lower than the oxygen partial pressure corresponding to the set value $V0_{SET}$ (for example, when hydrocarbons HC or the like are contained), the main pump cell 21 pumps oxygen into the first internal cavity 20 from the space outside the sensor element 101. Therefore, the value of the pump current Ip0 may be either positive or negative.

The drive control part 92 performs feedback control of the pump voltage Vp1 of the variable power supply 52 in the auxiliary pump cell 50 so that the voltage V1 in the oxygen-partial-pressure detection sensor cell 81 for auxiliary pump control is at a constant value (referred to as a set value $V1_{SET}$). The voltage V1 indicates the oxygen partial pressure in the vicinity of the auxiliary pump electrode 51, and therefore making the voltage V1 constant means that the oxygen partial pressure in the vicinity of the auxiliary pump electrode 51 is made constant. The oxygen partial pressure in the atmosphere in the second internal space 40 is thereby controlled to be a low partial pressure that does not substantially affect measurement of NOx.

At the same time, feedback control is performed to set the set value $V0_{SET}$ of the voltage V0 on the basis of the pump current Ip1 in the auxiliary pump cell 50 so that the pump current Ip1 is at a constant value (referred to as a set value $Ip1_{SET}$). Specifically, the pump current Ip1 is input, as a control signal, to the oxygen-partial-pressure detection sensor cell 80 for main pump control, and the voltage V0 therein is controlled to be the set value $V0_{SET}$set on the basis of the pump current Ip1 so that the oxygen partial pressure in the measurement-object gas introduced through the third diffusion-rate limiting part 30 into the second internal cavity 40 is controlled to have a gradient that is always constant. In use as the NOx sensor, the oxygen concentration in the second internal cavity 40 is maintained at a constant value of approximately 0.001 ppm by the action of the main pump cell 21 and the auxiliary pump cell 50. That is to say, the oxygen concentration in the measurement-object gas introduced through the fourth diffusion-rate limiting part 60 into the third internal cavity 61 is considered to be maintained at a constant value of approximately 0.001 ppm.

The drive control part 92 performs feedback control of the pump voltage Vp2 of the variable power supply 46 in the measurement pump cell 41 so that the voltage V2 detected in the oxygen-partial-pressure detection sensor cell 82 for measurement pump control is at a constant value (referred to as a set value $V2_{SET}$). In the measurement electrode 44, nitrogen oxide in the measurement-object gas is reduced ($2NO \rightarrow N_2 + O_2$) to generate oxygen. The generated oxygen is pumped out by the measurement pump cell 41 so that the voltage V2 becomes the set value $V2_{SET}$. The set value $V2_{SET}$ can be set as a value such that substantially all of NOx is decomposed at the measurement electrode 44. The set value $V2_{SET}$ can be set as a value such that the pump current Ip2 is at a limiting current.

The drive control part 92 may further perform a control to apply a pump voltage Vp3 by the power supply circuit 85 to the reference gas adjustment pump cell 84 to make a pump current Ip3 flow. By making a pump current Ip3 flow, pumping of oxygen into the reference gas chamber 43 (oxygen pump-in control) or pumping out of oxygen from the reference gas chamber 43 (oxygen pump-out control) may be performed. In the normal control, for example, a control to apply a predetermined pump voltage Vp3 or a control to apply a predetermined pump current Ip3 may be performed. When such a control is performed in the normal control, for example, the pump current Ip3 may be applied continuously or intermittently. The pump current Ip3 may be constant or may vary. When the oxygen pump-in control or the oxygen pump-out control is performed in the normal control, attention should be paid so that such a control is performed with virtually no influence on measurement accuracy.

As described later, at a time when the processing part 94 performs refresh processing, the drive control part 92 may stop the above-described normal control of each of the pump cells 21, 50, 41, and 84.

The storing part 93 stores in advance, a required amount of oxygen to be present in the reference gas chamber 43, at a time when oxygen concentration in a reference gas in the reference gas chamber 43 is a predetermined concentration. The predetermined concentration may be appropriately determined by a person skilled in the art, and may be an oxygen concentration equivalent to that in the air.

The storing part 93 may store in advance, as the required amount of the oxygen, for example, a required current integrated value of a current flowing between the pump electrode and the reference electrode 42 when the current is applied between the pump electrode and the reference electrode 42 to move oxygen of the required amount of the oxygen. The pump electrode is an electrode disposed at a position different from the reference gas chamber 43 and having a function of pumping oxygen. The pump electrode is normally disposed at a position exposed to the measurement-object gas. For example, the pump electrode may be disposed outside the base part 102, or may be disposed in the measurement-object gas flow cavity 15 (on an inner surface of the measurement-object gas flow cavity 15). The pump electrode may be, for example, the outer pump electrode 23, the inner main pump electrode 22, the auxiliary pump electrode 51, or the measurement electrode 44. In this embodiment, description will be made in the case where a current is applied between the outer pump electrode 23 and the reference electrode 42, as an example.

Figure 4:
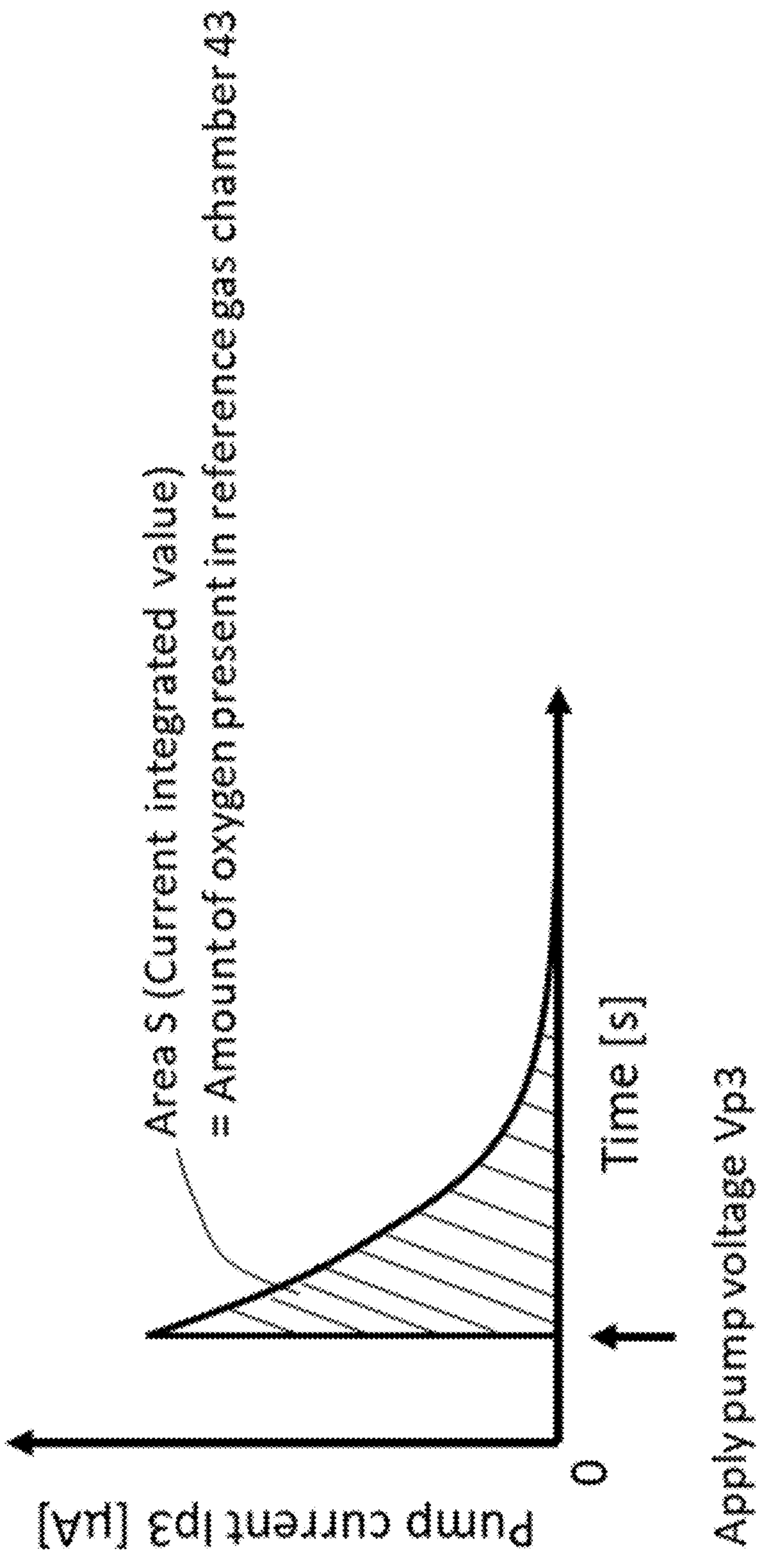
FIG. 4 is a schematic diagram showing an example of temporal change in a pump current Ip3 when oxygen is pumped out from a reference gas chamber 43.

Here, behavior of a current when oxygen is pumped out from the reference gas chamber 43 will be described. FIG. 4 is a schematic diagram showing an example of temporal change in the pump current Ip3 when oxygen is pumped out from the reference has chamber 43. In FIG. 4, the horizontal axis represents a time (seconds) and the vertical axis represents the pump current Ip3 (μA).

Referring to FIG. 4, the behavior of the pump current Ip3 will be explained when a predetermined pump voltage Vp3 is applied to the reference gas adjustment pump cell 84 (namely, between the outer pump electrode 23 and the reference electrode 42) to supply a pump current Ip3 so that oxygen is pumped out from the reference gas chamber 43. When a predetermined pump voltage Vp3 is applied to the reference gas adjustment pump cell 84, a pump current Ip3 flows so that oxygen is pumped out from the reference gas chamber 43. As oxygen is pumped out from the reference gas chamber 43, an amount of oxygen present in the reference gas chamber 43 decreases. As the amount of oxygen present in the reference gas chamber 43 decreases, a current value of the pump current Ip3 becomes smaller. And, when the amount of oxygen present in the reference gas chamber 43 reaches zero or nearly zero (substantially zero), the current value of the pump current Ip3 becomes zero, or nearly zero. An area S of a portion shown by oblique lines in FIG. 4 indicates a value of integrating the pump current Ip3 by time. This integrated value is referred to as a current integrated value (or, a current accumulated value). Since the pump current Ip3 indicates an amount of electric charge transferred per unit of time, the current integrated value (namely, the area S in FIG. 4) corresponds to an amount of electric charge of oxygen ions $O^{2-}$ transferred from the reference electrode 42 to the outer pump electrode 23. The amount of electric charge of the oxygen ions $O^{2-}$ corresponds to an amount of oxygen that was present in the reference gas chamber 43 before the pump current Ip3 starts to flow. Thus, the current integrated value (namely, the area S in FIG. 4) can be an index indicating the amount of oxygen that was present in the reference gas chamber 43.

Therefore, a current integrated value of the pump current Ip3 corresponding to a required amount of oxygen to be present in the reference gas chamber 43 may be obtained when oxygen concentration in a reference gas in the reference gas chamber 43 is a predetermined concentration, and the storing part 93 may store the obtained current integrated value (referred to as a required current integrated value). The required current integrated value is generally determined in accordance with the predetermined concentration of oxygen in the reference gas and a volume of the reference gas chamber 43.

The required current integrated value can be determined in, for example, the following manner. First, it is confirmed that oxygen concentration in a reference gas in the reference gas chamber 43 is a predetermined concentration, by conducting, for example, an oxygen concentration confirming step in production of the gas sensor 100 that will be described later. The confirmation of oxygen concentration is done in a state where the outer pump electrode 23 of the sensor element 101 is in contact with a gas having a known oxygen concentration (e.g., air). When oxygen concentration in the reference gas in the reference gas chamber 43 is a predetermined concentration, a predetermined pump voltage Vp3 is applied to the reference gas adjustment pump cell 84 (namely, between the outer pump electrode 23 and the reference electrode 42) by the power supply circuit 85 to make the pump current Ip3 flow so that oxygen present in the reference gas chamber 43 is pumped out from the reference electrode 42 to the outer pump electrode 23. The predetermined pump voltage Vp3 continues to be applied until the pump current Ip3 becomes at substantially zero, while the flowing pump current Ip3 and its time are acquired. Then, a time-integrated value (a required current integrated value) of the pump current Ip3, which corresponds to the area S in FIG. 4, is calculated.

For example, the storing part 93 may store in advance, as the required amount of the oxygen, for example, a required time when a predetermined current is applied between the pump electrode (e.g., the outer pump electrode 23) and the reference electrode 42 to move oxygen of the required amount of the oxygen. That is, the storing part 93 may store the required time for a current integrated value to reach the above-described required current integrated value by applying the predetermined current.

For example, the storing part 93 may store in advance, as the required amount of the oxygen, for example, a required current value when a current is applied between the pump electrode (e.g., the outer pump electrode 23) and the reference electrode 42 for a predetermined time to move oxygen of the required amount of the oxygen. That is, the storing part 93 may store the required current value for a current integrated value to reach the above-described required current integrated value by applying a current for the predetermined time. The processing part 94 performs refresh processing in which a current is applied between the pump electrode and the reference electrode 42 to pump out oxygen present in the reference gas chamber 43 from the reference gas chamber 43 so that oxygen present in the reference gas chamber 43 becomes at substantially zero, and then pump oxygen into the reference gas chamber 43 in the required amount of the oxygen which is stored in advance by the storing part 93. As described above, the pump electrode is an electrode disposed at a position different from the reference gas chamber 43. The pump electrode may be, for example, the outer pump electrode 23, the inner main pump electrode 22, the auxiliary pump electrode 51, or the measurement electrode 44. The refresh processing will be described later in detail.

Production of Gas Sensor

Hereinbelow, an example of a method for producing such a gas sensor 100 as described above will be described. The sensor element 101 can be produced by performing predetermined processing, circuit pattern printing and the like on each of unfired sheet-shaped molded products (so-called green sheets) containing an oxygen-ion-conductive solid electrolyte such as zirconia ($ZrO_2$) as a ceramic component, laminating these sheets, cutting the laminated body, and firing the resultant. Then, the gas sensor 100 incorporating the sensor element 101 is produced.

Hereinafter, description is made while taking the case of manufacturing the sensor element 101 composed of six layers shown in FIG. 2 as an example.

First, six green sheets containing an oxygen-ion-conductive solid electrolyte such as zirconia ($ZrO_2$) as a ceramic component are prepared. For manufacturing of the green sheets, a known molding method can be used. The six green sheets may all have the same thickness, or the thickness differs depending on the layer to be formed. In each of the six green sheets, sheet holes or the like for use in positioning at the time of printing or stacking are formed in advance by a known method such as a punching process with a punching apparatus (blank sheet). In the blank sheet for use as the spacer layer 5, penetrating parts such as internal cavities are also formed in the same manner. Also in the remaining layers, necessary penetrating parts are formed in advance.

The blank sheets for use as six layers, namely, the first substrate layer 1, the second substrate layer 2, the third substrate layer 3, the first solid electrolyte layer 4, the spacer layer 5, and the second solid electrolyte layer 6 are subjected to printing of various patterns required for respective layers and drying treatment. For printing of a pattern, a known screen printing technique can be used. Also as the drying treatment, a known drying means can be used.

After completing the printing and drying of diverse patterns for each of the six blank sheets by repeating these steps, contact bonding treatment of stacking the six printed blank sheets in a predetermined order while positioning with the sheet holes and the like, and contact bonding at a predetermined temperature and pressure condition to give a laminate is conducted. The contact bonding treatment is conducted by heating and pressurizing with a known laminator such as a hydraulic press. While the temperature, the pressure and the time of heating and pressurizing depend on the laminator being used, they may be appropriately determined to achieve excellent lamination.

The obtained laminate includes a plurality of sensor elements 101. The laminate is cut into units of the sensor element 101. The cut laminate is fired at a predetermined firing temperature to obtain the sensor element 101. The firing temperature may be such a temperature that the solid electrolyte forming the base part 102 of the sensor element 101 is sintered to become a dense product, and electrodes or the like maintains desired porosity. The firing is conducted, for example, at a firing temperature of about 1300 to 1500° C.

Then, the gas sensor 100 incorporating the sensor element 101 is produced. For example, the element sealing body 141 is attached to the sensor element 101 to seal and fix the sensor element 101, and the connector 150 and the lead wires 155 are attached to the rear end side of the sensor element 101 to be electrically connected with the connector electrodes such as the heater connector electrode 71. Further, the protection cover 130 is attached to the element scaling body 141 on the front end side of the sensor element 101. Further, the outer cylinder 148 is attached to the element scaling body 141 on the rear end side of the sensor element 101, and the lead wires 155 are drawn out from the outer cylinder 148. The control unit 90 and the sensor element 101 are connected via the lead wires 155. In this way, the gas sensor 100 is obtained.

The production process of the gas sensor 100 preferably includes, after the sensor element 101 or the gas sensor 100 is obtained, an oxygen concentration confirming step in which the oxygen concentration in the reference gas chamber 43 is confirmed and, if necessary, the oxygen concentration in the reference gas chamber 43 is adjusted. This step is performed in, for example, the following manner. First, the sensor element 101 is maintained at a predetermined driving temperature (e.g., 800° C.) and a voltage Vref of the sensor cell 83 is measured in a state where the outer pump electrode 23 of the sensor element 101 is in contact with a gas having a known oxygen concentration (e.g., air). Then, the oxygen concentration in the reference gas chamber 43 is derived based on the known oxygen concentration and the voltage Vref. Then, the oxygen concentration in the reference gas chamber 43 is confirmed to fall within a predetermined oxygen concentration range regarded as the same as the oxygen concentration in a reference gas. When the oxygen concentration in the reference gas chamber 43 falls outside the predetermined oxygen concentration range, a pump current Ip3 is applied by applying a pump voltage Vp3 from the power supply circuit 85 to the reference gas adjustment pump cell 84 to pump oxygen into the reference gas chamber 43 or pump out oxygen from the reference gas chamber 43. In this way, the oxygen concentration in the reference gas chamber 43 is adjusted to fall within the predetermined oxygen concentration range. The measurement of the voltage Vref and the adjustment of the oxygen concentration in the reference gas chamber 43 may be performed by the control unit 90 of the gas sensor 100 or by another device that is different from the control unit 90 and is connected to the sensor element 101.

At the time of measuring the voltage Vref in the oxygen concentration confirming step, a pump voltage Vp3 is not applied to the reference gas adjustment pump cell 84. Further, at the time of measuring the voltage Vref, it is preferred that a control to apply a current to the outer pump electrode 23 is not performed on the sensor element 101 to reduce a measurement error due to voltage drop of the outer pump electrode 23 and the reference electrode 42. Specifically, it is preferred that the operations of the main pump cell 21, the auxiliary pump cell 50, and the measurement pump cell 41 are stopped (the variable power supplies 24, 52, and 46 do not apply pump voltages Vp0, Vp1, and Vp2). Particularly, the pump current Ip0 flowing through the main pump cell 21 is relatively larger than the pump currents Ip1 and Ip2, and therefore the voltage drop of the outer pump electrode 23 is large. Therefore, among the main pump cell 21, the auxiliary pump cell 50, and the measurement pump cell 41, the operation of at least the main pump cell 21 is preferably stopped.

The production process of the gas sensor 100 preferably further includes, after the oxygen concentration confirming step, a required amount of oxygen storing step in which the storing part 93 stores a required amount of oxygen to be present in the reference gas chamber 43 when oxygen concentration in a reference gas in the reference gas chamber 43 is a predetermined concentration. This step is performed in, for example, the following manner. First, the sensor element 101 is maintained at a predetermined driving temperature (e.g., 800° C.), and the operations of the main pump cell 21, the auxiliary pump cell 50, the measurement pump cell 41, and the reference gas adjustment pump cell 84 in the normal control are stopped. The power supply circuit 85 applies a predetermined pump voltage Vp3 to the reference gas adjustment pump cell 84 (namely, between the outer pump electrode 23 and the reference electrode 42) to make the pump current Ip3 flow so that oxygen present in the reference gas chamber 43 is pumped out from the reference electrode 42 to the outer pump electrode 23. The power supply circuit 85 continues to apply the predetermined pump voltage Vp3 until the pump current Ip3 becomes at substantially zero, while the flowing pump current Ip3 and its time are acquired. Then, a time-integrated value of the pump current Ip3 (namely, a required current integrated value) corresponding to the area S in FIG. 4 is calculated.

The acquisition of the required amount of the oxygen (for example, the required current integrated value) described above is not affected by a gas atmosphere in contact with the outer pump electrode 23, unlike the case of the oxygen concentration confirming step described above. Therefore, the required amount of the oxygen may be obtained in the same gas atmosphere (for example, the air) as the oxygen concentration confirming step or a different gas atmosphere from the oxygen concentration confirming step.

The required amount of the oxygen (for example, the required current integrated value) may be obtained as described above in each individual gas sensor 100 produced and may be stored in the storing part 93 of the gas sensor 100. Alternatively, a typical required amount of oxygen (for example, a typical required current integrated value) may previously be obtained and stored in the storing parts 93 of a plurality of gas sensors 100. For example, the same required amount of oxygen (for example, the same required current integrated value) may be stored in gas sensors 100 having the same configuration or gas sensors 100 of the same production batch. Or, for example, a relationship between a volume of the reference gas chamber 43 and a required current integrated value is acquired or calculated in advance, and depending on a volume of the reference gas chamber 43 in each gas sensor 100, a required current integrated value corresponding to the each gas sensor 100 may be stored in the storing part 93. In these cases, the required amount of the oxygen storing step may be performed before the oxygen concentration confirming step.

The control unit 90 may perform the oxygen concentration confirming step during the use of the gas sensor 100 in a state where the oxygen concentration in a measurement-object gas is previously known. For example, when the measurement-object gas is exhaust gas from the internal combustion engine of a car or the like, the oxygen concentration in the measurement-object gas can be regarded as the same as the air at the time of fuel cutoff of the internal combustion engine, and therefore the same oxygen concentration confirming step as described above may be performed. And then, t the required amount of the oxygen storing step may be performed by acquiring the required amount of the oxygen (for example, the required current integrated value) as described above. It is more preferred that the required amount of the oxygen storing step is performed in the production process, that is, before shipment because refresh processing described later can be performed at any timing from the beginning of use of the gas sensor.

Refresh Processing

When the oxygen concentration in a reference gas changes for any reason in the gas sensor 100, the electric potential (reference potential) of the reference electrode 42 also changes in response to such a change. As a result, the voltages V0, V1, V2, and Vref in the respective sensor cells 80, 81, 82, and 83 detected using the reference electrode 42 as a reference change. Thus, the detection accuracy of the NOx concentration in a measurement-object gas may reduce. For example, in the present embodiment, the reference gas chamber 43 is a space substantially closed inside the base part 102. Therefore, flowing of gas into the reference gas chamber 43 from the outside of the sensor element 101 and flowing out of gas from the reference gas chamber 43 are both prevented. However, when, as described above, the voltages V0, V1, V2, and Vref in the respective sensor cells 80, 81, 82, and 83 are measured in the normal control, a minute current flows through each of the sensor cells 80, 81, 82, and 83 because of a voltage measuring circuit such as an electrometer. Therefore, it is considered that oxygen is electrochemically pumped into the reference gas chamber 43 or pumped out from the reference gas chamber 43 due to the minute current. As a result, the oxygen concentration in a reference gas in the reference gas chamber 43 may change.

The gas sensor according to the present invention can set (or, return) the oxygen concentration in the reference gas to a predetermined concentration by performing the refresh processing even if such a change in the oxygen concentration in a reference gas occurs. This makes it possible to prevent a reduction in the detection accuracy of the NOx concentration in a measurement-object gas to maintain high measurement accuracy. The refresh processing performed by the gas sensor according to the present invention will be described below in detail.

In the gas sensor 100, the processing part 94 performs the refresh processing of setting (or, returning) oxygen concentration in the reference gas to a predetermined concentration. The refresh processing keeps oxygen concentration in the reference gas at the predetermined concentration.

In the refresh processing, the processing part 94 makes a current flow between the pump electrode and the reference electrode 42 to pump out oxygen present in the reference gas chamber 43 from the reference gas chamber 43, thereby making the oxygen present in the reference gas chamber 43 at substantially zero. Then, the processing part 94 pumps oxygen into the reference gas chamber 43 in the required amount of the oxygen which is stored in advance by the storing part 93. By this processing, oxygen concentration in the reference gas chamber 43, namely, oxygen concentration in the reference gas can be set (or, returned) to the predetermined concentration.

That is, in the refresh processing, the processing part 94 performs: an oxygen pumping-out step of pumping out oxygen in the reference gas chamber 43 to make oxygen present in the reference gas chamber 43 at zero or substantially zero; and then an oxygen pumping-in step of pumping oxygen of the required amount of the oxygen into the reference gas chamber 43 to return oxygen concentration in the reference gas chamber 43 to the predetermined concentration.

That oxygen present in the reference gas chamber 43 is at substantially zero means that, for example, oxygen concentration in the reference gas chamber 43 is a concentration close to zero based on the predetermined concentration of the reference gas, such as 2% or less, 1% or less 0.5% or less, or 0.1% or less of the predetermined concentration. Alternatively, that oxygen present in the reference gas chamber 43 is at substantially zero means that an amount of oxygen in the reference gas chamber 43 is an amount close to zero based on the required amount of the oxygen, such as 2% or less, 1% or less 0.5% or less, or 0.1% or less of the required amount of the oxygen.

Figure 5:
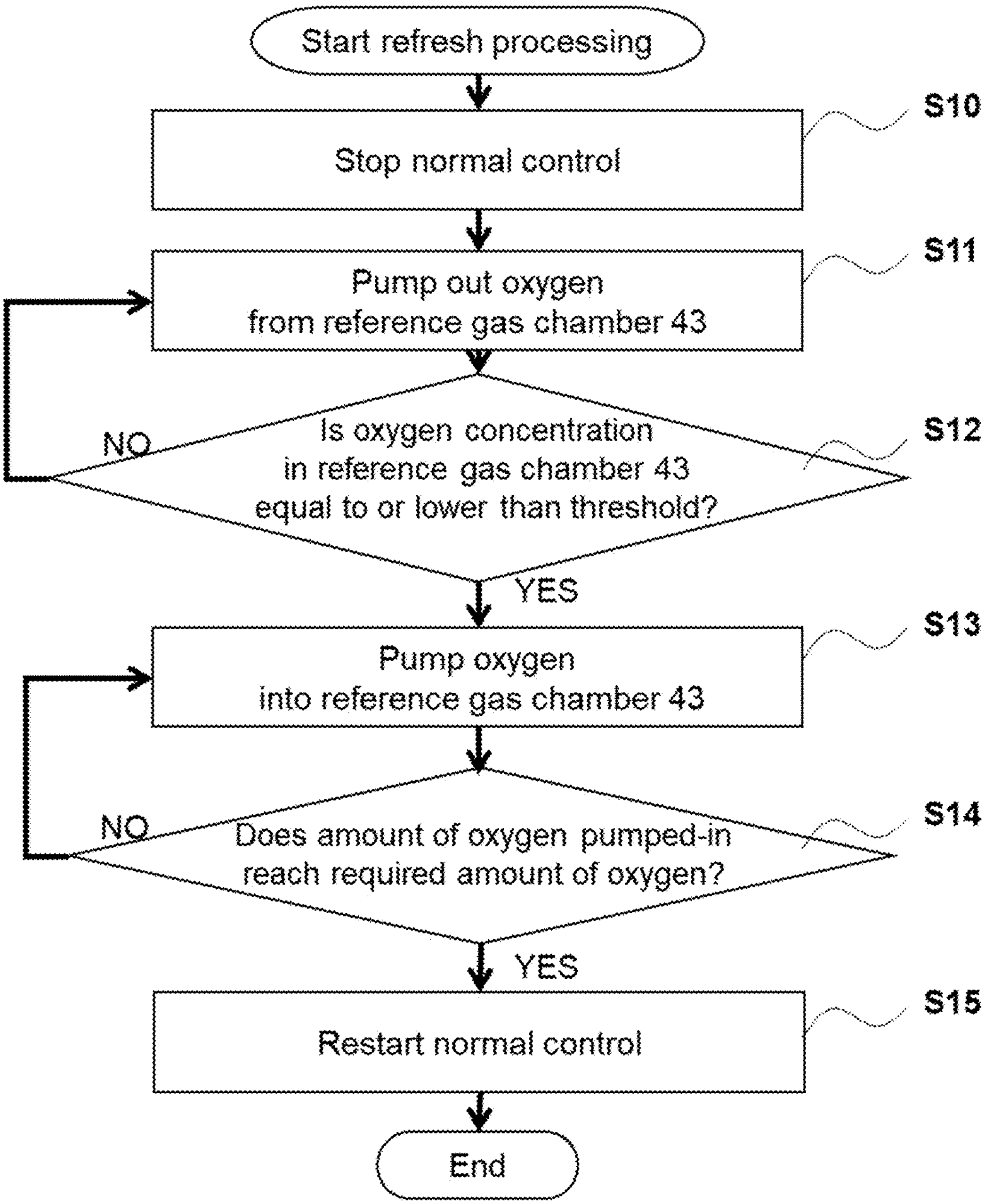
FIG. 5 is a flowchart showing an example of refresh processing.

In this embodiment, the processing part 94 apply the pump current Ip3 to the reference gas adjustment pump cell 84 (namely, between the outer pump electrode 23 and the reference electrode 42) to perform pumping-out of oxygen from the reference gas chamber 43, or pumping-in of oxygen into the reference gas chamber 43. FIG. 5 is a flowchart showing an example of refresh processing.

When the refresh processing starts, the drive control part 92 stops the normal control (step S10). Specifically, all the pump controls such as a control to feed back a pump voltage Vp0 of the main pump cell 21 so that the voltage V0 is at a set value $V0_{SET}$, a control to feed back a pump voltage Vp1 of the auxiliary pump cell 50 so that the voltage V1 is at a set value $V1_{SET}$, and a control to feed back a pump voltage Vp2 of the measurement pump cell 41 so that the voltage V2 is at a set value $V2_{SET}$ are stopped. That is, controls other than a control to maintain the sensor element 101 at a predetermined temperature by the heater 72 are not performed. Therefore, during the execution of the refresh processing, the measurement of the NOx concentration in a measurement-object gas is stopped.

Then, the processing part 94 pumps out oxygen from the reference gas chamber 43 (step S11). Specifically, for example, the processing part 94 applies the pump voltage Vp3 to the reference gas adjustment pump cell 84 (namely, between the outer pump electrode 23 and the reference electrode 42) by the power supply circuit 84 to make the pump current Ip3 flow. The applied pump voltage Vp3 may be constant, or may be varied continuously or stepwise.

Then, the processing part 94 determines whether or not oxygen concentration in the reference gas in the reference gas chamber 43 is equal to or lower than a threshold (step S12). The threshold may be appropriately determined by a person skilled in the art. The threshold of the oxygen concentration in the reference gas chamber 43 may be determined so that oxygen present in the reference gas chamber 43 is at zero or substantially zero. Alternatively, the threshold may be determined with respect to an amount of oxygen present in the reference gas chamber 43.

When oxygen concentration in the reference gas is higher than the threshold in step S12, step S11 is conducted. That is, the processing part 94 continues to pump out oxygen from the reference gas chamber 43. On the other hand, when oxygen concentration in the reference gas is equal to or lower than the threshold, the processing part 94 stops pumping-out of oxygen from the reference gas chamber 43, and pumps oxygen into the reference gas chamber 43 (step S13). That is, the oxygen pumping-out step is finished and the oxygen pumping-in step is started. Specifically, for example, the processing part 94 applies a pump voltage Vp3 reverse in positive and negative of the voltage in step S11 to the reference gas adjustment pump cell 84 (namely, between the outer pump electrode 23 and the reference electrode 42) to make the pump current Ip3 flow in a direction of pumping oxygen into the reference gas chamber 43. The pump voltage Vp3 applied in step S13 may be constant, or may be varied continuously or stepwise. Further, the pump voltage Vp3 applied in step S13 may have the same absolute value as the pump voltage Vp3 applied in step S11, or different in the absolute value from the pump voltage Vp3 applied in step S11.

The processing part 94 reads out the required amount of oxygen from the storing part 93. Then, the processing part 94 determines whether or not an amount of oxygen pumped-in in step S13 reaches the required amount of the oxygen (step S14). Here, the amount of the oxygen pumped-in indicates a total amount (or, integrated amount or accumulated amount) of oxygen pumped-in during from when pumped-in of oxygen into the reference gas chamber 43 is started until when determination in step S14 is done.

When the amount (total amount) of oxygen pumped-in does not reach the required amount of the oxygen at the time of determination in step S14, namely, when the amount (total amount) of oxygen pumped-in is less than the required amount of the oxygen at the time of determination in step S14, step S13 is conducted. That is, the processing part 94 continues to pump oxygen into the reference gas chamber 43. On the other hand, when the amount (total amount) of oxygen pumped-in reaches the required amount of the oxygen, the processing part 94 stops pumping-in of oxygen into the reference gas chamber 43, and allows the drive control part 92 to restart the normal control (step S15). Then, the refresh processing is completed.

Figure 6:
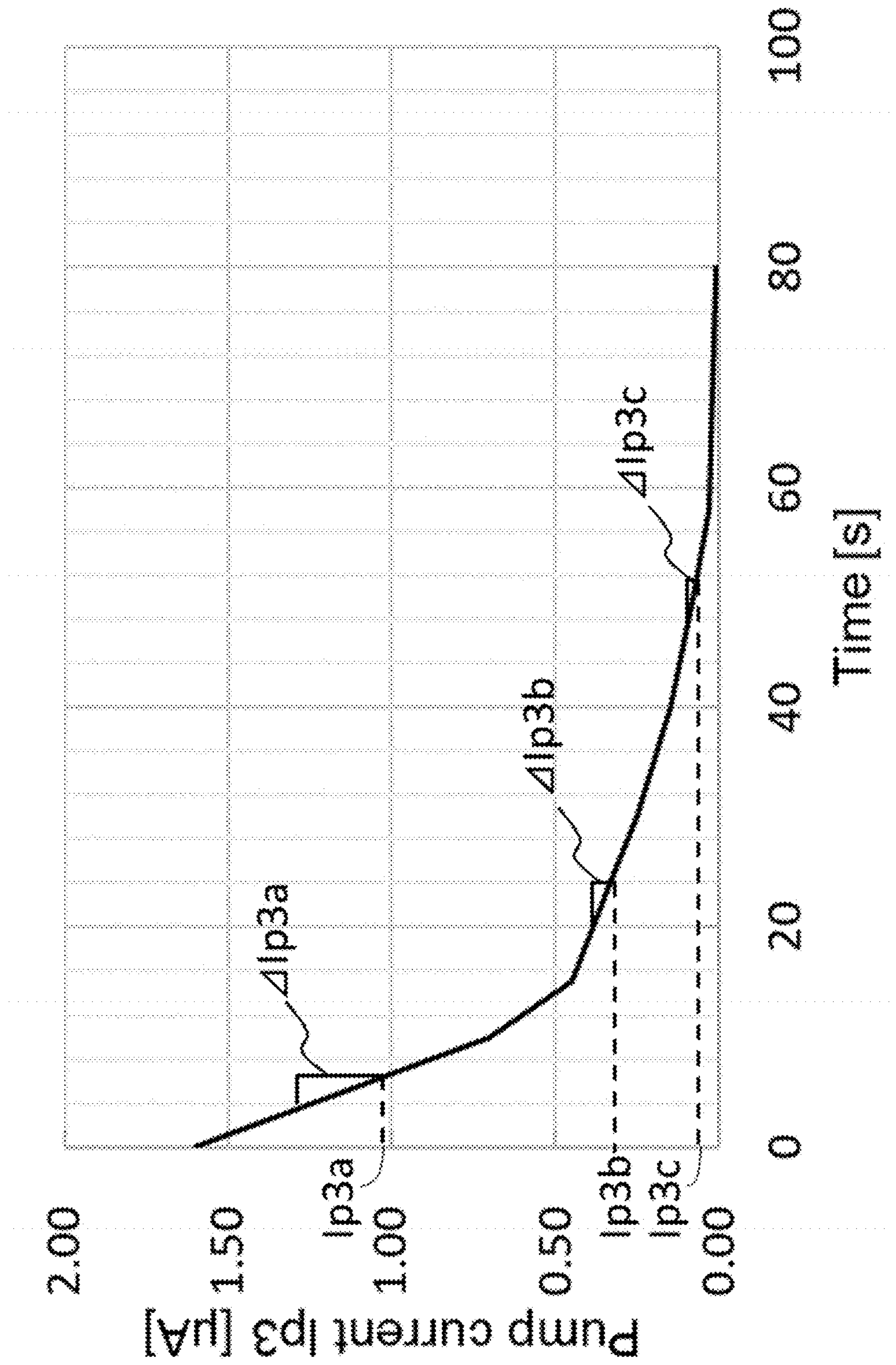
FIG. 6 is a schematic diagram showing an example of temporal change in the pump current Ip3 at oxygen pumping-out step (step S11 in FIG. 5) in the refresh processing.

More detailed description will be done about the oxygen pumping-out step in the refresh processing. FIG. 6 is a schematic diagram showing an example of temporal change in the pump current Ip3 at the oxygen pumping-out step (step S11 in FIG. 5). In FIG. 6, the horizontal axis represents a time (seconds) and the vertical axis represents the pump current Ip3 (μA). In the oxygen pumping-out step, as the description for FIG. 4 made above, a current value of the pump current Ip3 becomes smaller as the amount of oxygen present in the reference gas chamber 43 decreases. FIG. 6 shows that the pump current Ip3 decreases as the time elapses (i.e.., Ip3*a*>Ip3*b*>Ip3*c*). Then, the pump current Ip3 becomes at zero or a sufficiently small value close to zero when oxygen concentration in the reference gas chamber 43 becomes at zero or an amount close to zero (substantially zero).

For example, the processing part 94 may apply a predetermined voltage (in this embodiment, the pump voltage Vp3) between the pump electrode (in this embodiment, the outer pump electrode 23) and the reference electrode 42 to make a current (in this embodiment, the pump current Ip3) flow, and may pump out oxygen present in the reference gas chamber 43 from the reference gas chamber 43 until the current becomes at a predetermined value or less. The predetermined value (referred to as a threshold A) of the current may be appropriately determined by a person skilled in the art, and may be set to zero or a value close to zero. When the predetermined value (namely, the threshold A) is set to such a value, it is possible to pump out oxygen from the reference gas chamber 43 until oxygen in the reference gas chamber 43 becomes at substantially zero. As a result, the oxygen concentration in the reference gas in the reference gas chamber 43 can be more accurately made (or returned) to a predetermined concentration by the refresh processing. The predetermined value (namely, the threshold A) may be, for example, 1.0 μA or less, 0.5 μA or less, 0.25 μA or less, or 0.1 μA or less.

Further, as shown in FIG. 6, a change amount per time (a time change amount) of the pump current Ip3 decreases as the time elapses. A slope of the graph in FIG. 6 becomes smaller as the time elapses. Namely, ΔIp3*a*>ΔIp3*b*>ΔIp3*c* in FIG. 6. Therefore, for example, the processing part 94 may apply a predetermined voltage (in this embodiment, the pump voltage Vp3) between the pump electrode (in this embodiment, the outer pump electrode 23) and the reference electrode 42 to make a current (in this embodiment, the pump current Ip3) flow, and may pump out oxygen present in the reference gas chamber 43 from the reference gas chamber 43 until a change amount per time (a time change amount) in the current becomes at a predetermined value or less. The predetermined value (referred to as a threshold B)

of the time change amount in the current may be appropriately determined by a person skilled in the art, and may be set to zero or a value close to zero. When the predetermined value (namely, the threshold B) is set to such a value, it is possible to pump out oxygen from the reference gas chamber 43 until oxygen in the reference gas chamber 43 becomes at substantially zero. As a result, oxygen concentration in the reference gas in the reference gas chamber 43 can be more accurately made (or returned) to a predetermined concentration by the refresh processing. The predetermined value (namely, the threshold B) may be, for example, 0.1 μA/s or less, 0.05 μA/s or less, 0.02 μA/s or less, or 0.01 μA/s or less.

Figure 7:
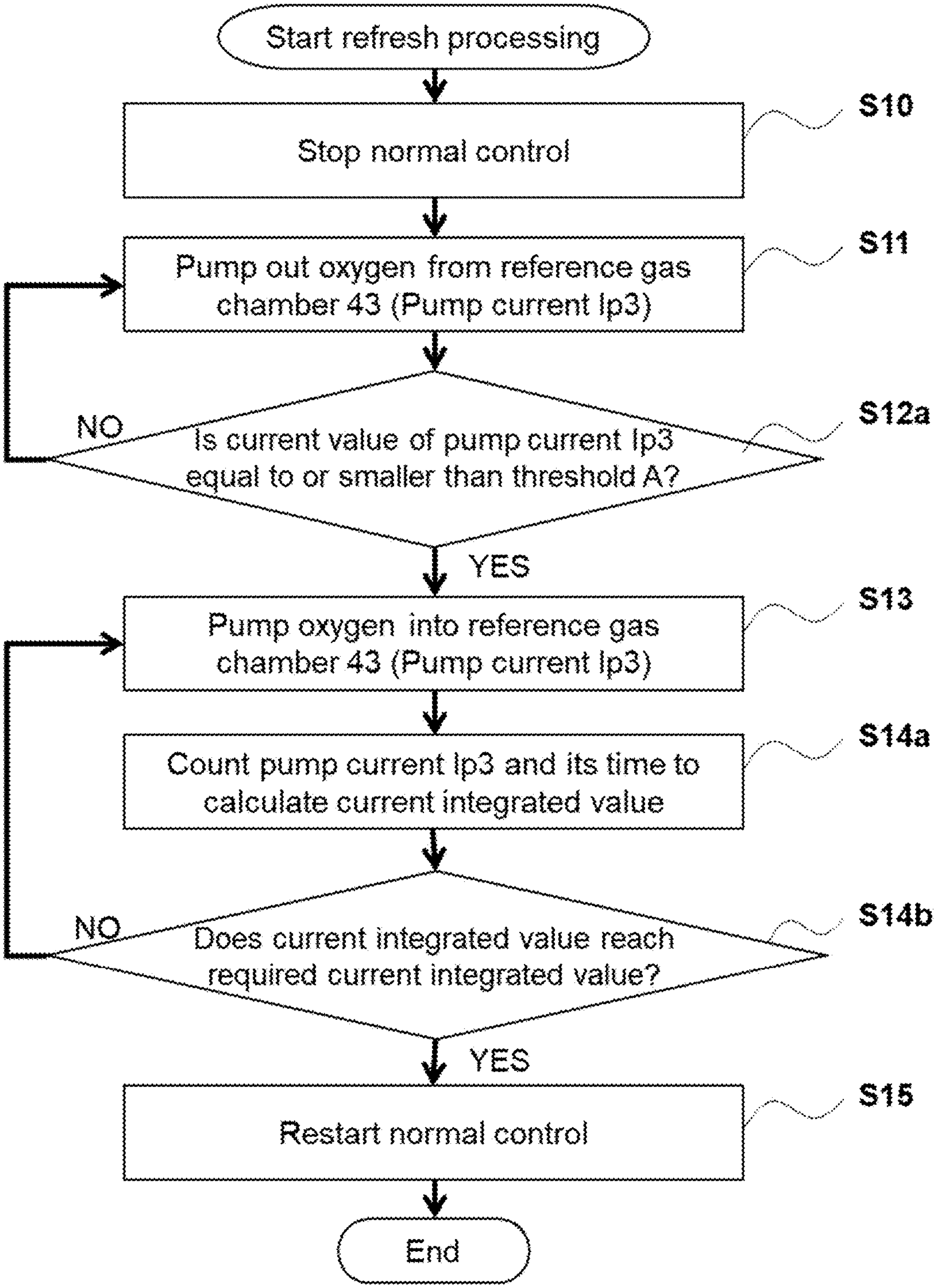
FIG. 7 is a flowchart showing a specific example of refresh processing.

FIG. 7 is a flowchart of the refresh processing, showing a specific example of the oxygen pumping-out step and the oxygen pumping-in step. In FIG. 7, the same step numbers as in FIG. 5 denote the same steps, and therefore the description thereof will not be repeated. It is to be noted that a specific example of the oxygen pumping-in step (steps S14*a* and S14*b*) will be described later.

In the example shown in FIG. 7, as the oxygen pumping-out step, the processing part 94 applies a predetermined pump voltage Vp3 between the outer pump electrode 23 and the reference electrode 42 to make a pump current Ip3 flow, and pumps out oxygen present in the reference gas chamber 43 from the reference gas chamber 43 until the pump current Ip3 becomes at a predetermined value (namely, a threshold A) or less.

In this case, the processing part 94 determines whether or not a current value of the pump current Ip3 that pumps out oxygen from the reference gas chamber 43 is equal to or smaller than the predetermined value (namely, the threshold A) (step S12*a*). When the current value of the pump current Ip3 is larger than the threshold A in step S12*a*, step S11 is conducted. That is, the processing part 94 continues to pump out oxygen from the reference gas chamber 43. On the other hand, when the current value of the pump current Ip3 is equal to or smaller than the threshold A, the processing part 94 stops pumping-out of oxygen from the reference gas chamber 43, and pumps oxygen into the reference gas chamber 43 (step S13).

Figure 8:
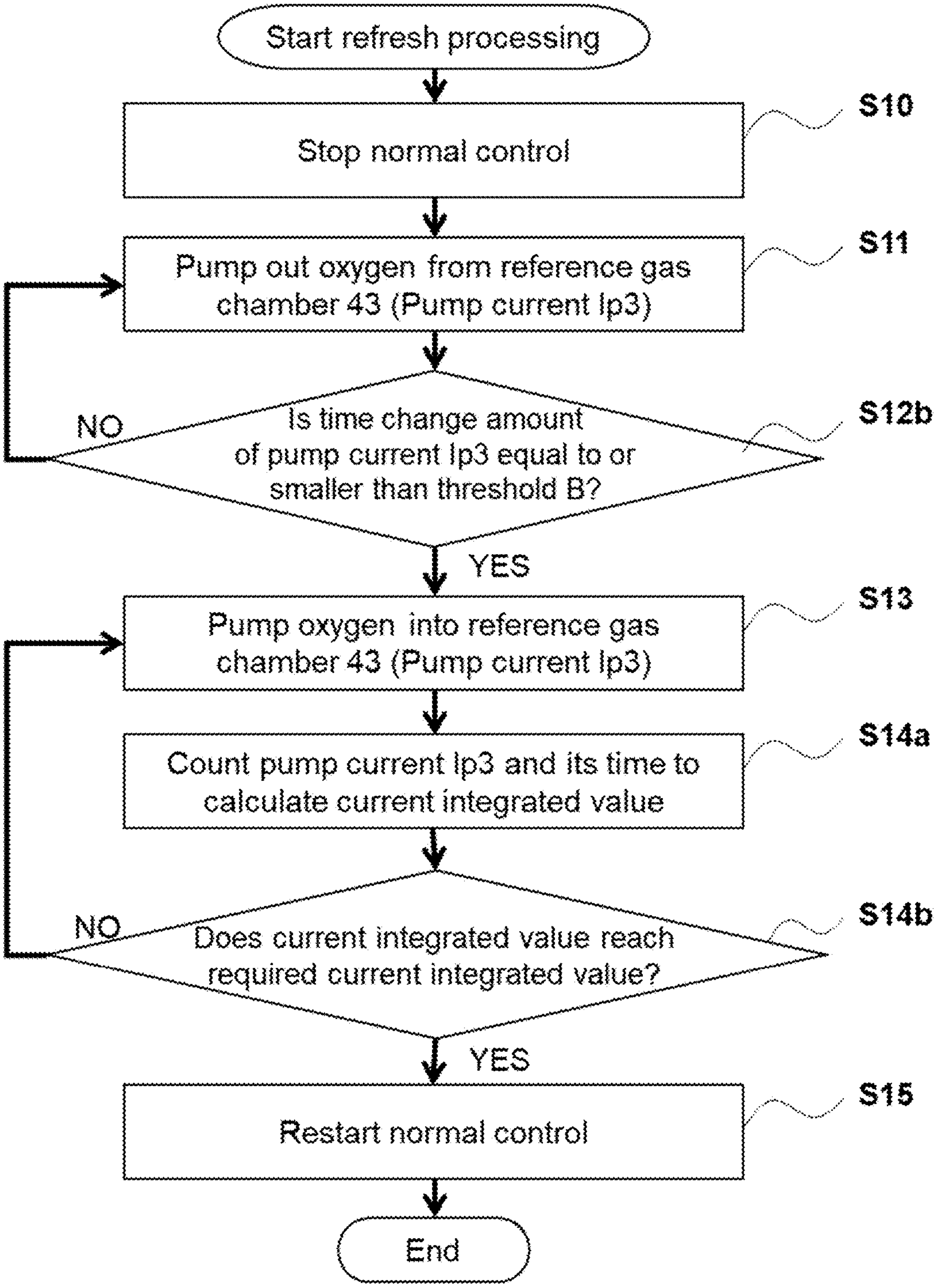
FIG. 8 is a flowchart showing another specific example of refresh processing.

Further, FIG. 8 is a flowchart of the refresh processing, which shows a specific example different from the oxygen pumping-in step shown in FIG. 7. In FIG. 8, the same step numbers as in FIG. 7 denote the same steps.

In the example shown in FIG. 8, as the oxygen pumping-out step, the processing part 94 applies a predetermined pump voltage Vp3 between the outer pump electrode 23 and the reference electrode 42 to make a pump current Ip3 flow, and pumps out oxygen present in the reference gas chamber 43 from the reference gas chamber 43 until a change amount per time (a time change amount) in the current becomes at a predetermined value (namely, a threshold B) or less.

In this case, the processing part 94 determines whether or not a time change amount in a current value of the pump current Ip3 that pumps out oxygen from the reference gas chamber 43 is equal to or smaller than the predetermined value (namely, the threshold B) (step S12*b*). When the time change amount in the current value of the pump current Ip3 is larger than the threshold B in step S12*b*, step S11 is conducted. That is, the processing part 94 continues to pump out oxygen from the reference gas chamber 43. On the other hand, when the time change amount in the current value of the pump current Ip3 is equal to or smaller than the threshold B, the processing part 94 stops pumping-out of oxygen from the reference gas chamber 43, and pumps oxygen into the reference gas chamber 43 (step S13).

Next, the oxygen pumping-in step in FIG. 7 and FIG. 8 will be described. In this case, the storing part 93 stores in advance, the above-described required current integrated value. The required current integrated value is, for example, an integrated value of the pump current Ip3 flowing between the outer pump electrode 23 and the reference electrode 42, when the pump current Ip3 is applied between the outer pump electrode 23 and the reference electrode 42 to move oxygen of the required amount of the oxygen. As the oxygen pumping-in step, the processing part 94 applies a current between the outer pump electrode 23 and the reference electrode 42 until an integrated value of the pump current Ip3 flowing between the outer pump electrode 23 and the reference electrode 42 reaches the required current integrated value to pump oxygen in the required amount of the oxygen into the reference gas chamber 43.

In this case, the processing part 94 counts a current value and a time of the current value of the pump current Ip3 pumping oxygen into the reference gas chamber 43, and calculates a current integrated value at the present moment from start of applying the pump current Ip3 (step S14*a*). For example, when the pump current Ip3 is measured periodically, the processing part 94 may sequentially add a product multiplying the pump current Ip3 at each measurement by a measurement period to calculate the current integrated value. The processing part 94 reads out the required current integrated value from the storing part 93. Then, the processing part 94 determines whether or not the calculated current integrated value reaches the required current integrated value (step S14*b*). When the current integrated value does not reach the required current integrated value at the time of determination in step S14*b*, namely, when the current integrated value is less than the required current integrated value at the time of determination in step S14*b*, step S13 is conducted. That is, the processing part 94 continues to pump oxygen into the reference gas chamber 43. On the other hand, when the current integrated value reaches the required current integrated value, the processing part 94 stops pumping-in of oxygen into the reference gas chamber 43, and allows the drive control part 92 to restart the normal control (step S15).

As described above, in the refresh processing, the oxygen pumping-out step is done at first to make oxygen present in the reference gas chamber 43 at zero or substantially zero. And then, oxygen is pumped into the reference gas chamber 43 in the required amount of the oxygen that is stored in the storing part 93 in advance. For example, the pump current Ip3 is applied until an integrated value of the pump current Ip3 reaches the required current integrated value. Such refresh processing is not affected by composition of a measurement-object gas (such as oxygen concentration and NOx concentration). Therefore, the refresh processing can be performed regardless of oxygen concentration and NOx concentration in the measurement-object gas. Further, the refresh processing does not require that oxygen concentration and NOx concentration in the measurement-object gas are known.

The refresh processing may be performed at any timing. For example, the refresh processing may be performed at a predetermined time interval (e.g., every 50 hours or every 100hours). Alternatively, for example, the refresh processing may be performed when an operator inputs a start command of the refresh processing. Alternatively, for example, the refresh processing may be performed at the time of a predetermined event such as the activation of the gas sensor 100.

A volume of the reference gas chamber 43 corresponds to a volume of a reference gas that can be present in the reference gas chamber 43. Therefore, when an amount of oxygen in the reference gas chamber 43 changes during the use of the gas sensor 100, the larger the volume of the reference gas chamber 43, the relatively smaller the change in the oxygen concentration in the reference gas due to the change in the amount of oxygen in the reference gas chamber 43. The smaller the volume of the reference gas chamber 43, the larger the change in the oxygen concentration in the reference gas due to the change in the amount of oxygen in the reference gas chamber 43. Therefore, for example, a cycle for performing the refresh processing may be determined based on a volume of the reference gas chamber 43. The cycle for performing the refresh processing may be determined with respect to a cumulative time (a cumulative driving time) during which the gas sensor 100 is driven. For example, when the volume of the reference gas chamber 43 is large, the cycle for performing the refresh processing may be prolonged (or, an interval at which the refresh processing is performed may be prolonged). When the volume of the reference gas chamber 43 is small, the cycle for performing the refresh processing may be shortened (or, the interval at which the refresh processing is performed may be shortened).

The cycle for performing the refresh processing may be appropriately determined in accordance with intended use or required accuracy of the gas sensor 100, a configuration of the sensor element 101, and the like. For example, the cycle of the refresh processing may be set to a value that is approximately proportional to the volume of the reference gas chamber 43. The cycle may be determined so that the refresh processing is performed, for example,

- every 100 hours of the cumulative driving time when the volume of the reference gas chamber 43 is 0.036 $mm^3$;
- every 200 hours of the cumulative driving time when the volume of the reference gas chamber 43 is 0.06 $mm^3$;
- every 800 hours of the cumulative driving time when the volume of the reference gas chamber 43 is 0.26 $mm^3$; or,
- every 1500 hours of the cumulative driving time when the volume of the reference gas chamber 43 is 0.50 $mm^3$.

As described above, the gas sensor 100 according to the present embodiment can set (or, return) the oxygen concentration in the reference gas in the reference gas chamber 43 to the predetermined concentration by performing the refresh processing. This refresh processing is not affected by composition of a measurement-object gas (such as oxygen concentration and NOx concentration). Thus, unlike the oxygen concentration confirming step in the production process described above, the refresh processing does not require that oxygen concentration in the measurement-object gas is known. Therefore, the oxygen concentration in the reference gas in the reference gas chamber 43 can be set (or, returned) to the predetermined concentration at any timing during the use of the gas sensor 100 also in cases other than a case where the concentration of oxygen or NOx in a measurement-object gas is known or irrespective of the concentrations of them. As a result, it is possible to prevent a reduction in the detection accuracy of the NOx concentration in a measurement-object gas to maintain high measurement accuracy.

The gas sensor 100 for detecting the NOx concentration in a measurement-object gas has been described above as an example of the embodiment according to the present invention, but the present invention is not limited to this embodiment. The present invention may include various gas sensors different in configuration as long as the object of the present invention is achieved, that is, as long as a reduction in the detection accuracy of a target gas to be measured in a measurement-object gas is prevented to maintain high detection accuracy.

In the above embodiment, the required current integrated value is obtained by applying the pump current Ip3 to the reference gas adjustment pump cell 84 (namely, between the outer pump electrode 23 and the reference electrode 42) so that the oxygen in the reference gas chamber 43 becomes at substantially zero when the oxygen concentration in the reference gas in the reference gas chamber 43 is the predetermined concentration. However, the present invention is not limited to this. When obtaining the required current integrated value, a current may be applied between a pump electrode disposed at a position different from the reference gas chamber 43 and the reference electrode 43. For example, the required current integrated value may be obtained by applying a current between the inner main pump electrode 22 and the reference electrode 42. The required current integrated value may be obtained by applying a current between the auxiliary pump electrode 51 and the reference electrode 42. The required current integrated value may be obtained by applying a current between the measurement electrode 44 and the reference electrode 42. Since the required current integrated value corresponds to an amount of oxygen to be present in the reference gas chamber 43, the obtained required current integrated value is substantially the same regardless of which pump electrode is used.

Further, the required current integrated value may be determined in, for example, the following manner. First, a pump voltage is applied between the pump electrode (the outer pump electrode 23, the inner main pump electrode 22, the auxiliary pump electrode 51 or the measurement electrode 44) and the reference electrode 42 to make a pump current flow in a direction of pumping out oxygen from the reference gas chamber 43, and oxygen in the reference gas chamber 43 is pumped out so that oxygen present in the reference gas chamber 43 becomes at zero or substantially zero. Then, oxygen is pumped into the reference gas chamber 43 in a state where the outer pump electrode 23 of the sensor element 101 is in contact with a gas having a known oxygen concentration (e.g., air). That is, a predetermined pump voltage is applied between the pump electrode and the reference electrode 42 to make a pump current flow in a direction of pumping oxygen into the reference gas chamber 43. A voltage Vref of the sensor cell 83 (namely, between the outer pump electrode 23 and the reference electrode 42) is measured, and based on the known oxygen concentration and the voltage Vref, the pump current is applied to pump oxygen into the reference gas chamber 43 until oxygen concentration in the reference gas chamber 43 reaches a predetermined concentration. The required current integrated value may be obtained by calculating an integrated value of the pump current in this case. When oxygen is pumped into the reference gas chamber 43 while the voltage Vref of the sensor cell 83 is measured as described above, it is preferred that the inner main pump electrode 22, the auxiliary pump electrode 51 or the measurement electrode 44 is used as the pump electrode.

In the above embodiment, the outer pump electrode 23 is used as the pump electrode in each of the processes of acquisition of the required current integrated value, oxygen pumping-out step in the refresh processing, and oxygen pumping-in step in the refresh processing, but the pump electrode is not limited to this. Any one or more of these processes may be performed by applying a current between a pump electrode different from that used in other processes and the reference electrode 42. Electrodes used as the pump electrodes may be different in all of the processes.

In the above-described embodiment, all the pump controls are stopped in step S10 in the refresh processing, but step S10 is not limited thereto. The drive control part 92 stops at least any one or more pump cells of the main pump cell 21, the auxiliary pump cell 50 and the measurement pump cell 41. Since the refresh processing includes a process of pumping out oxygen in the reference gas chamber 43 from the reference gas chamber 43 to make oxygen present in the reference gas chamber 43 at zero or substantially zero, it is preferred to stop pump controls referring to reference potential of the reference electrode 42. All the pump controls may be preferably stopped as in the case of the embodiment described above.

In the above embodiment, the pump voltage Vp3 is applied to the reference gas adjustment pump cell 84 to make the pump current Ip3 flow in each of step S11 and step S13 in the refresh processing, but step S11 and step S13 is not limited thereto. For example, the processing part 94 may apply a pump current Ip3 by a current supply. In the normal control, a control of applying a pump voltage to make a pump current flow in each of the pump cells 21, 50, 41 (and 84) is performed, but the normal control is not limited thereto. In one or more of these pump cells 21, 50, 41 (and 84), a control of applying a current by a current supply may be performed.

In the above-described embodiment, the reference gas chamber 43 is a space closed inside the base part 102. However, the reference gas chamber 43 is not limited thereto. For example, the reference gas chamber 43 may entirely or partially be filled with a porous material such as alumina.

Figure 9:
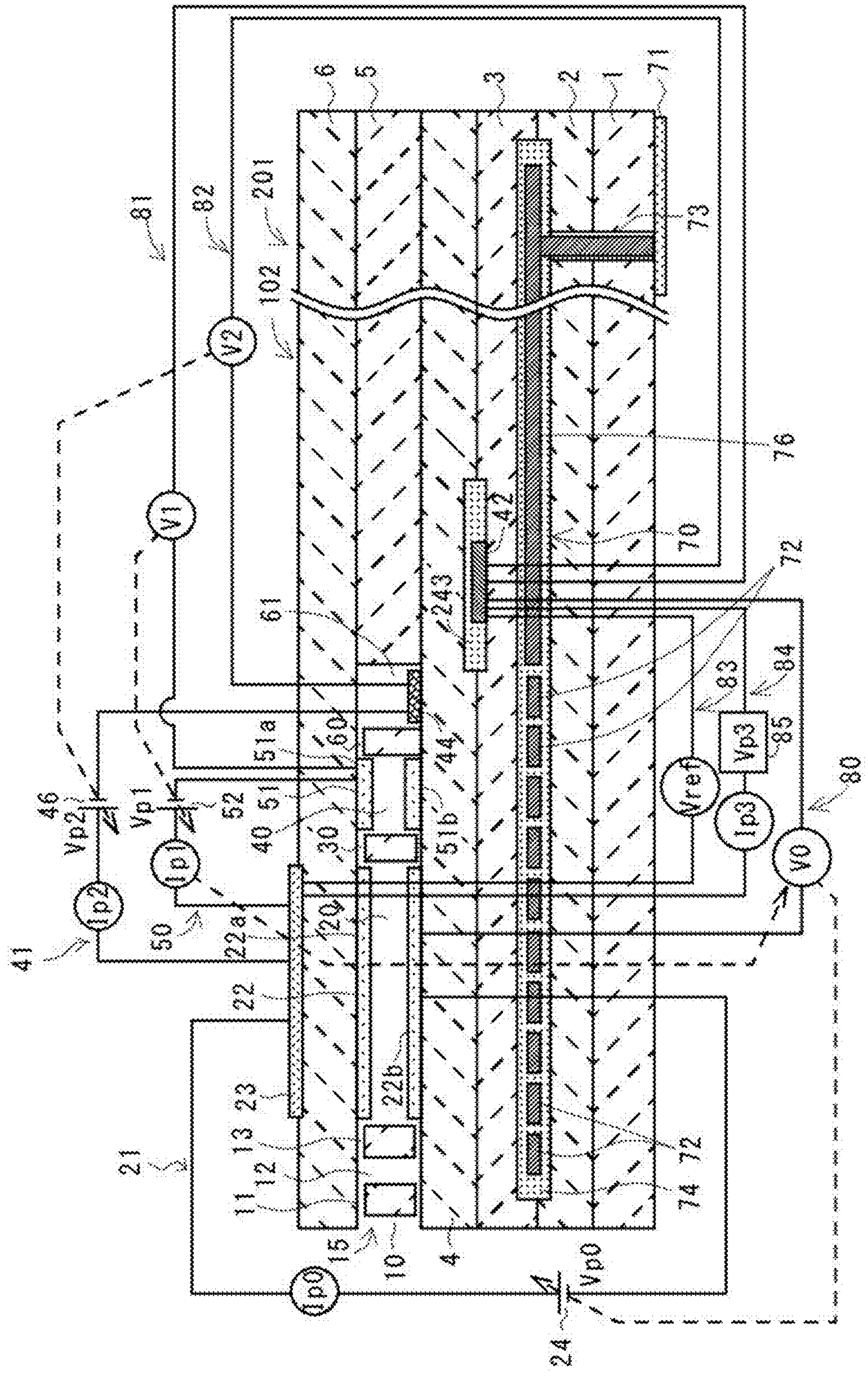
FIG. 9 is a vertical sectional schematic view in a longitudinal direction of a sensor element 201 of a Variation.

FIG. 9 is a vertical sectional schematic view in a longitudinal direction of a sensor element 201 of a Variation in which the reference gas chamber is filled with a porous material. In the sensor element 201, the reference gas chamber 243 is provided between the upper surface of the third substrate layer 3 and the lower surface of the first solid electrolyte layer 4 to cover the reference electrode 42. The reference gas chamber 243 is closed inside the base part 102, and filled with the porous material. As described above, a volume of the reference gas chamber 43 means a volume of a reference gas that can be present in the reference gas chamber 43. Thus, in the case of such a reference gas chamber 243, a volume of the reference gas chamber 243 is to be a value considering a size of the reference gas chamber 243 and a porosity of the porous material filling the reference gas chamber 243. In the sensor element 201, the volume of the reference gas chamber 243 is approximately a total volume of pores in the reference gas chamber 243. The configuration of the sensor element 201 shown in FIG. 9 other than the above is substantially the same as that of the sensor element 101 described with reference to FIG. 2.

Figure 10:
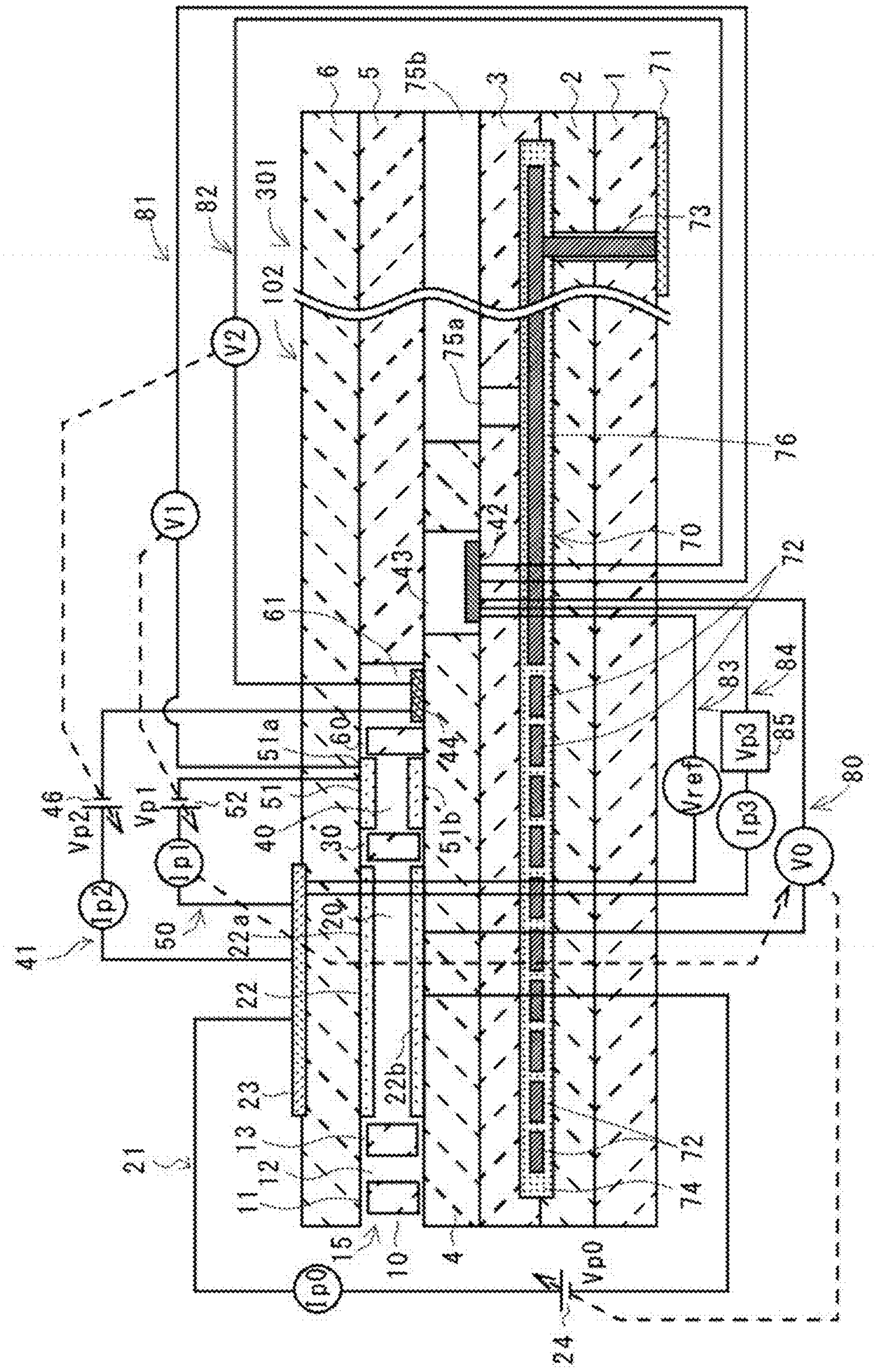
FIG. 10 is a vertical sectional schematic view in a longitudinal direction of a sensor element 301 of a Variation.

The sensor element may further include a pressure relief vent. FIG. 10 is a vertical sectional schematic view in a longitudinal direction of a sensor element 301 of a Variation that includes a pressure relief vent. In the sensor element 301, a pressure relief space 75*b* that is open to the rear end surface of the sensor element 301 is formed in the first solid electrolyte layer 4 rearward of the reference gas chamber 43. Further, the pressure relief vent 75*a* is formed so that an upper surface of the heater insulating layer 74 and the pressure relief space 75*b* communicate with each other. The pressure relief vent 75*a* is formed as a hole penetrating through the third substrate layer 3. The pressure relief vent 75*a* plays a role of mitigating an increase in internal pressure due to temperature rise in the heater insulating layer 74. The pressure relief space 75*b* and the pressure relief vent 75*a* does not communicate with the reference gas chamber 43. The configuration of the sensor element 301 shown in FIG. 10 other than the above is substantially the same as that of the sensor element 101 described with reference to FIG. 2.

In the gas sensor 100 of the above embodiment, as shown in FIG. 2, the sensor element 101 has a structure in which three internal cavities, the first internal cavity 20, the second internal cavity 40, and the third internal cavity 61 are provided and the inner main pump electrode 22, the auxiliary pump electrode 51, and the measurement electrode 44 are respectively disposed in these internal cavities. However, the structure of the sensor element 101 is not limited thereto. For example, the sensor element 101 may have a structure in which two internal cavities, the first internal cavity 20 and the second internal cavity 40 are provided, the inner main pump electrode 22 is disposed in the first internal cavity 20, and the auxiliary pump electrode 51 and the measurement electrode 44 are disposed in the second internal cavity 40. In this case, for example, a porous protective layer covering the measurement electrode 44 may be formed as a diffusion-rate limiting part between the auxiliary pump electrode 51 and the measurement electrode 44.

In the above embodiment, the gas sensor 100 detects the NOx concentration in a measurement-object gas. However, the target gas to be measured is not limited to NOx. The sensor element of the gas sensor 100 may have a structure using an oxygen-ion-conductive solid electrolyte. For example, the target gas to be measured may be oxygen $O_2$, or an oxide gas other than NOx (e.g., carbon dioxide $CO_2$, water $H_2O$). Alternatively, the target gas to be measured may be a non-oxide gas such as ammonia $NH_3$. When the target gas to be measured is a non-oxide gas, the non-oxide gas is converted to an oxide gas (for example, in the case of ammonia $NH_3$, $NH_3$ is converted to NO), and a measurement-object gas containing the converted oxide gas is introduced into the third internal cavity 61. At the measurement electrode 44, the converted oxide gas in the measurement-object gas is reduced so that oxygen is generated. The target gas to be measured can be detected by acquiring the generated oxygen as the pump current Ip2 in the measurement pump cell 41. The conversion from the non-oxide gas to the oxide gas can be performed by allowing at least one of the inner main pump electrode 22 and the auxiliary pump electrode 51 to function as a catalyst.

EXAMPLES

Hereinafter, further description is made using Examples. The present invention is not limited to the following Examples.

Example 1

The gas sensor 100 shown in FIGS. 1 to 3 was produced in accordance with the above-described production method of the gas sensor 100 as Example 1. In Example 1, the control unit 90 was set to perform the refresh processing according to the flowchart in FIG. 8. The refresh processing was to be performed after a lapse of 200 hours of a driving time from the start of driving the gas sensor 100. In the refresh processing, a threshold B in pumping out of oxygen was set to 0.05 μA/s. A required current integrated value in pumping-in of oxygen was 3.0 μA.s.

Comparative Example 1

A gas sensor 100 of Comparative Example 1 was produced in the same manner as in Example 1 except that the control unit 90 was set not to perform the refresh processing.

Evaluation on Stability of NOx Output

Stability of a NOx output was evaluated in the following manner for each of the produced gas sensors of Example 1 and Comparative Example 1.

Initially, the gas sensors of Example 1 and Comparative Example 1 were attached to a gas chamber. Each of the gas sensors was driven and each NOx output was continuously measured for a long time in a state where the inside of the gas chamber was maintained in a model gas atmosphere. A gas atmosphere of the model gas was NO=0 ppm, $O_2$=0%, $H_2O$=3%, and $N_2$ (the remainder). Each of gas concentrations was in a unit of a volume basis. The measurement was continued for 400 hours.

Figure 11:
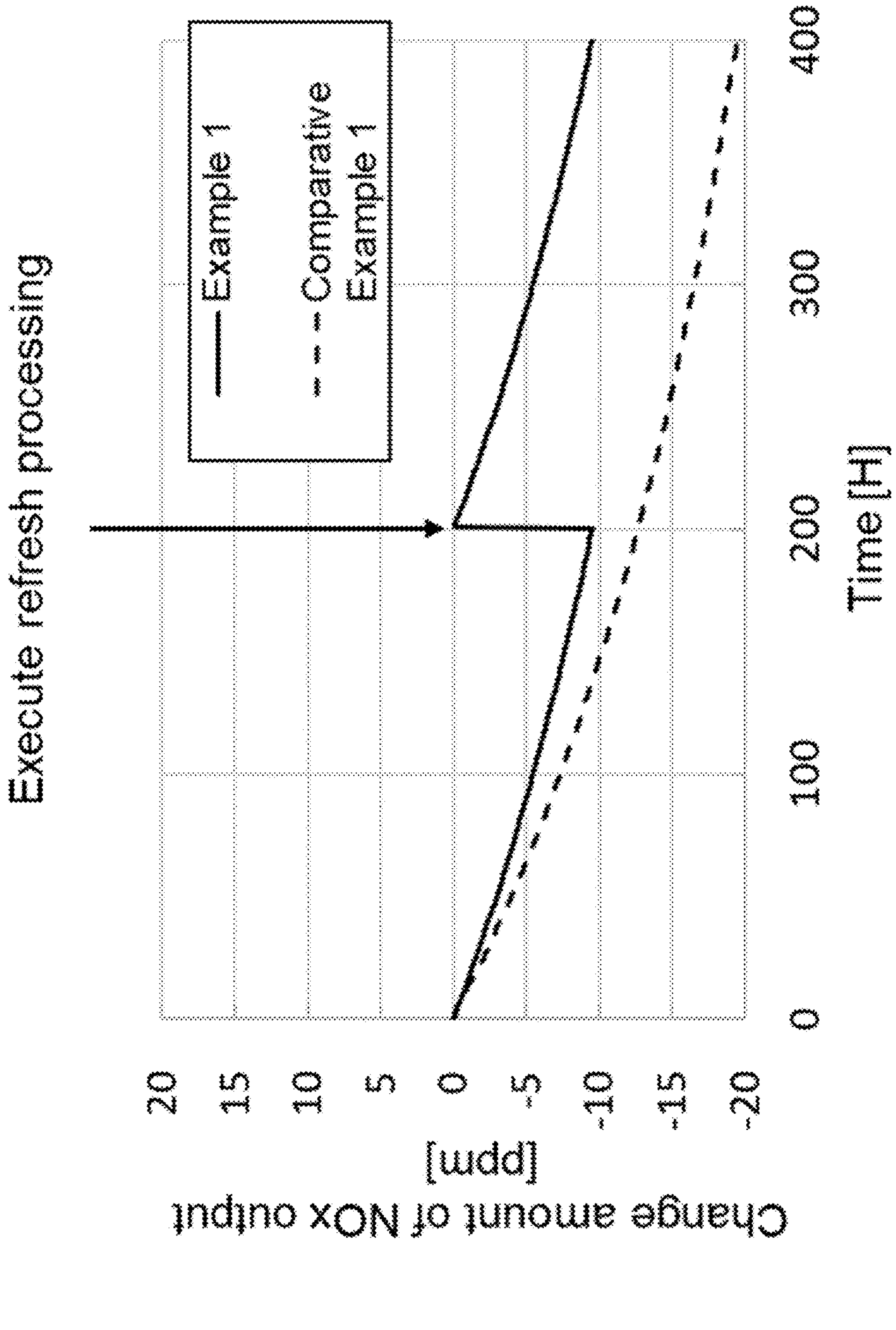
FIG. 11 is a graph showing an evaluation result of stability of a NOx output in each of Example 1 and Comparative Example 1.

FIG. 11 is a graph showing an evaluation result of stability of NOx outputs in Example 1 and Comparative Example 1. In FIG. 11, the horizontal axis represents a measurement time (hours; H) and the vertical axis represents a change amount of a NOx output (ppm). The change amount of the NOx output indicates a deviation of the NOx output from a value to be output in accordance with NOx concentration. In the above-described evaluation on the stability of the NOx output, the value to be output in accordance with NOx concentration is 0 ppm since NO concentration in the model gas is 0 ppm. Therefore, a value of the NOx output and the change amount of the NOx output are consequently the same value.

As shown in FIG. 11, the NOx outputs changed gradually with time in both of Example 1 and Comparative Example 1. In Example 1, it was confirmed that the change amount of the NOx output became at substantially zero when the refresh processing was executed. As a result, it was confirmed that the change amount of the NOx output in Example 1 could be suppressed to be small over a long period of time compared with Comparative Example 1. As such, the change amount of the NOx output can be returned to substantially zero every time of performing the refresh processing. As a result, it is considered to be possible to prevent a reduction in the detection accuracy of the target gas to be measured to maintain high detection accuracy.

As has been described above, according to the present invention, it is possible to set (or, returned) the oxygen concentration in the reference gas around the reference electrode to the predetermined concentration at any timing during the use of the gas sensor also in cases other than a case where the oxygen concentration in a measurement-object gas is known or irrespective of the oxygen concentration. As a result, it is possible to prevent a reduction in the detection accuracy of the target gas to be measured to maintain high detection accuracy.

EXPLANATION OF REFERENCE SIGNS IN THE DRAWINGS

1: first substrate layer; 2: second substrate layer; 3: third substrate layer; 4: first solid electrolyte layer; 5: spacer layer; 6: second solid electrolyte layer; 10: gas inlet; 11: first diffusion-rate limiting part; 12: buffer space; 13: second diffusion-rate limiting part; 15: measurement-object gas flow cavity; 20: first internal cavity; 21: main pump cell; 22: inner main pump electrode; 22*a*: ceiling electrode portion (of the inner main pump electrode); 22*b*: bottom electrode portion (of the inner main pump electrode); 23: outer pump electrode; 24: variable power supply (of the main pump cell); 30: third diffusion-rate limiting part; 40: second internal cavity; 41: measurement pump cell; 42: reference electrode; 43, 243: reference gas chamber; 44: measurement electrode; 46: variable power supply (of the measurement pump cell); 50: auxiliary pump cell; 51: auxiliary pump electrode; 51*a*: ceiling electrode portion (of the auxiliary pump electrode); 51*b*: bottom electrode portion (of the auxiliary pump electrode); 52: variable power supply (of the auxiliary pump cell); 60: fourth diffusion-rate limiting part; 61: third internal cavity; 70: heater part; 71: heater connector electrode; 72: heater; 73: through hole; 74: heater insulating layer; 75*a*: pressure relief vent; 75*b*: pressure relief space; 76: heater lead; 80: oxygen-partial-pressure detection sensor cell for main pump control; 81: oxygen-partial-pressure detection sensor cell for auxiliary pump control; 82: oxygen-partial-pressure detection sensor cell for measurement pump control; 83: sensor cell; 84: reference gas adjustment pump cell; 85: power supply circuit; 90: control unit; 91: control part; 92: drive control part; 93: storing part; 94: processing part; 100: gas sensor; 101, 201, 301: sensor element; and 102: base part.

What is claimed is:

1. A gas sensor for detecting a target gas to be measured in a measurement-object gas, the gas sensor comprising a sensor element and a control unit for controlling the sensor element, wherein the sensor element comprises:

a base part in an elongated plate shape, including an oxygen-ion-conductive solid electrolyte layer;

a measurement-object gas flow cavity for introduction and flow of the measurement-object gas, formed from one end part in a longitudinal direction of the base part;

a reference gas chamber formed inside the base part, and being separated from the measurement-object gas flow cavity and closed inside the base part;

a reference electrode disposed in the reference gas chamber; and a pump electrode disposed at a position different from the reference gas chamber, and the control unit comprises:

a memory storing in advance, a value of a required amount of oxygen to be present in the reference gas chamber at a time at which oxygen concentration in a reference gas in the reference gas chamber is a predetermined concentration; and a processor performing refresh processing in which a current is applied between the pump electrode and the reference electrode to pump out oxygen present in the reference gas chamber from the reference gas chamber, and then pump oxygen into the reference gas chamber in the required amount of the oxygen which is stored in advance by the memory.

2. The gas sensor according to claim 1, wherein the memory stores in advance, as the value of the required amount of the oxygen, a required current integrated value of a current flowing between the pump electrode and the reference electrode when the current is applied between the pump electrode and the reference electrode to move oxygen of the required amount of the oxygen, and in the refresh processing, the processor pumps out oxygen present in the reference gas chamber from the reference gas chamber, and then applies the current between the pump electrode and the reference electrode until an integrated value of the current flowing between the pump electrode and the reference electrode reaches the required current integrated value to pump oxygen into the reference gas chamber in the required amount of the oxygen.

3. The gas sensor according to claim 1, wherein the memory stores in advance, as the value of the required amount of the oxygen, a required time when a predetermined current is applied between the pump electrode and the reference electrode to move oxygen of the required amount of the oxygen, and in the refresh processing, the processor pumps out oxygen present in the reference gas chamber from the reference gas chamber, and then applies the predetermined current between the pump electrode and the reference electrode for the required time to pump oxygen into the reference gas chamber in the required amount of the oxygen.

4. The gas sensor according to claim 1, wherein the memory stores in advance, as the value of the required amount of the oxygen, a required current value when a current is applied between the pump electrode and the reference electrode for a predetermined time to move oxygen of the required amount of the oxygen, and in the refresh processing, the processor pumps out oxygen present in the reference gas chamber from the reference gas chamber, and then applies the current of the required current value between the pump electrode and the reference electrode for the predetermined time to pump oxygen into the reference gas chamber in the required amount of the oxygen.

5. The gas sensor according to claim 1, wherein in the refresh processing, the processor applies a predetermined voltage between the pump electrode and the reference electrode to make the current flow, and pumps out oxygen present in the reference gas chamber from the reference gas chamber until the current becomes at a predetermined value or less.

6. The gas sensor according to claim 1, wherein in the refresh processing, the processor applies a predetermined voltage between the pump electrode and the reference electrode to make the current flow, and pumps out oxygen present in the reference gas chamber from the reference gas chamber until a change amount per time in the current becomes at a predetermined value or less.

7. The gas sensor according to claim 1, wherein a cycle for performing the refresh processing is determined based on a volume of the reference gas chamber.

* * * * *